(12) United States Patent
Smejkal et al.

(10) Patent No.: US 9,643,938 B2
(45) Date of Patent: May 9, 2017

(54) PROCESS FOR THE PREPARATION OF SUBSTITUTED CYCLOSERINES

(71) Applicant: Syngenta Participations AG, Basel (CH)

(72) Inventors: Tomas Smejkal, Stein (CH); Helmars Smits, Stein (CH); Christian Lothschuetz, Munchwilen (CH); Miroslav Terinek, Munchwilen (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/307,386

(22) PCT Filed: Apr. 30, 2015

(86) PCT No.: PCT/EP2015/059612
§ 371 (c)(1),
(2) Date: Oct. 28, 2016

(87) PCT Pub. No.: WO2015/166094
PCT Pub. Date: Nov. 5, 2015

(65) Prior Publication Data
US 2017/0044116 A1  Feb. 16, 2017

(30) Foreign Application Priority Data
Apr. 30, 2014 (EP) ..................................... 14166654

(51) Int. Cl.
*C07D 261/04* (2006.01)
(52) U.S. Cl.
CPC ................................. *C07D 261/04* (2013.01)
(58) Field of Classification Search
CPC .................................................. C07D 261/04
USPC ....................................................... 548/244
See application file for complete search history.

(56) References Cited

FOREIGN PATENT DOCUMENTS

| DE | 2408324 | 8/1974 |
|---|---|---|
| KR | 2012/0131646 A | 12/2012 |
| WO | 96/30381 A1 | 10/1996 |

OTHER PUBLICATIONS

Friggeri, Laura et al: "Pharmacophore Assessment Through 3-D QSAR . . . ", Journal of Chemical Infomration and Modeling, vol. 53, 2013, pp. 1463-1474.
Charles H. Stammer et al: "Cycloserine Derivates", J. Med. Chem., vol. 13, No. 5, 1970, pp. 1013-1015.
Myoung Goo Kim et al: "N(2)-Substituted D, L-Cycloserine Derivates", Journal of Antibiotics, vol. 56, No. 2, 2003, pp. 160-168.
Di Felice P et al: "A New Stereoselective . . . " Tetrahedron Asymmetry, Pergamon Press Ltd, Oxford, GB, vol. 10, No. 11, Jun. 4, 1999, pp. 2191-2201.
Darwish et al—Synthesis of the Antifungal Agent Norneoenactin A—J Org Chem 1993 vol. 58 (p. 6072-6075).
Wada et al—Structure of 4-Aminolactivinic Acid—ACTA Crystallographica Section C—Crystal Structure Communications vol. C43, No. 9 1987—(p. 1786-1788).
International Search Report for International Patent Application No. PCT/EP2015/059612 dated Jul. 3, 2015.
European Search Report for EP Patent Application No. 14166654.5 issued on Nov. 4, 2014.

*Primary Examiner* — Kristin Vajda
(74) *Attorney, Agent, or Firm* — R. Kody Jones

(57) ABSTRACT

The present invention relates to processes for the preparation of substituted cycloserine compounds of formula (I) wherein $R^1$ is $C_1$-$C_8$alkyl, $C_1$-$C_8$haloalkyl, $C_3$-$C_6$cycloalkyl, aryl or aryl substituted by one to five $R^{11}$, or aryl-$C_1$-$C_4$alkylene or aryl-$C_1$-$C_4$alkylene substituted by one to five $R^{11}$; and each $R^{11}$ is independently $C_1$-$C_4$alkyl, $C_1$-$C_4$haloalkyl, $C_1$-$C_4$alkoxy, $C_1$-$C_4$haloalkoxy, cyano or halogen; The invention also relates to intermediates produced by the processes. Compounds of formula (I) are useful intermediates for the production of compounds in the agricultural and pharmaceutical fields.

5 Claims, No Drawings

PROCESS FOR THE PREPARATION OF SUBSTITUTED CYCLOSERINES

RELATED APPLICATION INFORMATION

This application is a 371 of International Application No. PCT/EP2015/059612, filed 30 Apr. 2015, which claims priority to EP Patent Application No. 14166654.5, filed 30 Apr. 2014, the contents of which are incorporated by reference herein.

The present invention relates to novel methods of producing 2-substituted cycloserines (4-amino-isoxazolidin-3-one) and intermediates useful in the preparation of 2-substituted cycloserines.

2-substituted cycloserines are useful intermediates in the preparation of certain insecticidally active compounds, for example those described in WO2011/067272 and WO2012/163959. Some cycloserines are also used as broad spectrum antibiotics.

2-substituted cycloserines are prepared in WO2011/067272 according to the method described in Chem. Pharm. Bull. 2002, 50(4) 554-557, which involves alkylation of the parent cycloserine or cycloserine derivative such as a tert-butyloxycarbonyl. Similar procedures are described in Tet. Lett. 2012, 2564-2567.

The main drawbacks of the known methods of alkylating cycloserines include the formation of isomeric by-products arising from O-alkylation instead of the desired N-alkylation, and possible epimerisation of the cycloserine stereocentre, particularly when strongly basic conditions are employed. There are also limitations imposed by the low reactivity and accessibility of the corresponding alkylation reagents.

It has been found that the insecticides described in WO2011/067272 and WO2012/163959 are more efficacious when the cycloserine moiety is present in the molecule with the D stereo-configuration, making it particularly desirable to find methods of derivatising cycloserine that reduce epimerisation.

Although regioselective derivatisation of cycloserine has been described in Tet. Lett. 2012, 2564-2567, special equipment was needed and this method is not appropriate for commercial scale production.

Methods of derivatising cycloserines have now surprisingly been found that allow preparation of 2-substituted cycloserines without requiring cycloserine starting material. These methods also provide further advantages by avoiding the need for protecting groups and allowing preparation of 2-substituted cycloserines with a defined stereo configuration.

In an aspect the invention provides a process for the preparation of a compound of formula (I)

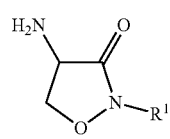

(I)

wherein
$R^1$ is $C_1$-$C_8$alkyl, $C_1$-$C_8$haloalkyl, aryl or aryl substituted by one to five $R^{11}$, or aryl-$C_1$-$C_4$alkylene or aryl-$C_1$-$C_4$alkylene substituted by one to five $R^{11}$; and
each $R^{11}$ is independently $C_1$-$C_4$alkyl, $C_1$-$C_4$haloalkyl, $C_1$-$C_4$alkoxy, $C_1$-$C_4$haloalkoxy, cyano or halogen;

comprising
a. reacting a compound of formula (II) or a salt thereof

(II)

wherein $R^1$ is as defined for the compound of formula (I) with a compound of formula (III)

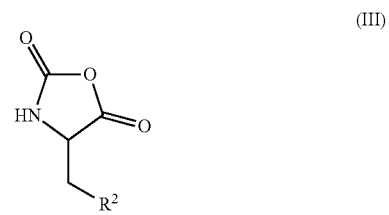

(III)

wherein $R^2$ is a leaving group, for example halogen, $C_1$-$C_8$alkylsulfonyloxy, $C_1$-$C_8$haloalkylsulfonyloxy, $C_1$-$C_8$arylsulfonyloxy or $C_1$-$C_8$arylsulfonyloxy substituted by one to five $R^{11}$, or a phosphonate ester; and each $R^{11}$ is as defined for the compound of formula (I) in the presence of a base.

Examples of suitable and preferred bases for performing the step a. are given below.

In an aspect the invention provides a process for the preparation of a compound of formula (I)

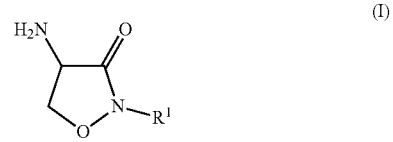

(I)

wherein
$R^1$ is $C_1$-$C_8$alkyl, $C_1$-$C_8$haloalkyl, aryl or aryl substituted by one to five $R^{11}$, or aryl-$C_1$-$C_4$alkylene or aryl-$C_1$-$C_4$alkylene substituted by one to five $R^{11}$; and
each $R^{11}$ is independently $C_1$-$C_4$alkyl, $C_1$-$C_4$haloalkyl, $C_1$-$C_4$alkoxy, $C_1$-$C_4$haloalkoxy, cyano or halogen;
comprising
a-1. reacting the compound of formula (II) with the compound of formula (III) to produce the compound of formula (IV) or a salt thereof

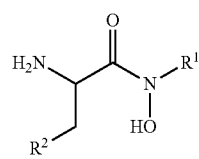

(IV)

wherein $R^1$ and $R^2$ are as defined for the compound of formula (I) and formula (III) in the presence of a suitable acid; and
a-2. converting the compound of formula (IV) to the compound of formula (I) in the presence of a suitable base.

Examples of suitable acids used in the step a-1 and preferred acids used in the step a-1 are given below.

Examples of suitable bases used in the step a-2 and preferred bases used in the step a-2 are given below.

In a further aspect the invention provides a process for the preparation of a compound of formula (IV) comprising performing step a-1 as defined above. In a further aspect the invention provides a process for the preparation of a compound of formula (I)

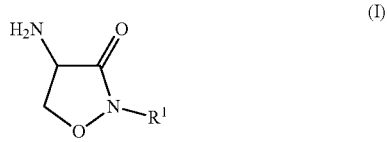
(I)

wherein
$R^1$ is $C_1$-$C_8$alkyl, $C_1$-$C_8$haloalkyl, aryl or aryl substituted by one to five $R^{11}$, or aryl-$C_1$-$C_4$alkylene or aryl-$C_1$-$C_4$alkylene substituted by one to five $R^{11}$; and
each $R^{11}$ is independently $C_1$-$C_4$alkyl, $C_1$-$C_4$haloalkyl, $C_1$-$C_4$alkoxy, $C_1$-$C_4$haloalkoxy, cyano or halogen;
comprising the step a-2
a-2. converting the compound of formula (IV)

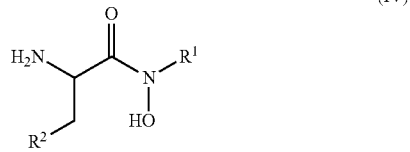
(IV)

wherein
$R^1$ is $C_1$-$C_8$alkyl, $C_1$-$C_8$haloalkyl, aryl or aryl substituted by one to five $R^{11}$, or aryl-$C_1$-$C_4$alkylene or aryl-$C_1$-$C_4$alkylene substituted by one to five $R^{11}$;
$R^2$ is $C_1$-$C_8$alkylsulfonyloxy, $C_1$-$C_8$haloalkylsulfonyloxy, $C_1$-$C_8$arylsulfonyloxy or $C_1$-$C_8$arylsulfonyloxy substituted by one to five $R^{11}$, or a phosphonate ester; and
each $R^{11}$ is independently $C_1$-$C_4$alkyl, $C_1$-$C_4$haloalkyl, $C_1$-$C_4$alkoxy, $C_1$-$C_4$haloalkoxy, cyano or halogen; to the compound of formula (I) in the presence of a suitable base.

In a further aspect the invention provides a process for the preparation of a compound of formula (I) comprising performing step a-2. as defined above. In a further aspect the invention provides a process for the preparation of a compound of formula (IV)

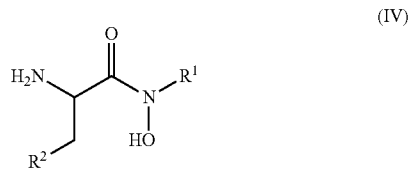
(IV)

wherein $R^1$ and $R^2$ are as defined for the compound of formula (I) and formula (III) comprising reacting according to the step a-1. the compound of formula (II) with the compound of formula (III) to produce the compound of formula (IV)

In one aspect the present invention relates to a process for the preparation of a compound of formula (I)

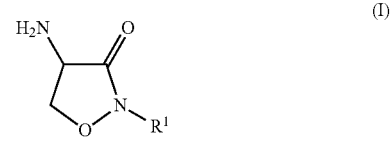
(I)

wherein
$R^1$ is $C_1$-$C_8$alkyl, $C_1$-$C_8$haloalkyl, aryl or aryl substituted by one to five $R^{11}$, or aryl-$C_1$-$C_4$alkylene or aryl-$C_1$-$C_4$alkylene substituted by one to five $R^{11}$; and
each $R^{11}$ is independently $C_1$-$C_4$alkyl, $C_1$-$C_4$haloalkyl, $C_1$-$C_4$alkoxy, $C_1$-$C_4$haloalkoxy, cyano or halogen;
comprising
reacting a compound of formula (II) or a salt thereof

(II)

wherein $R^1$ is as defined for the compound of formula (I); with a compound of formula (III)

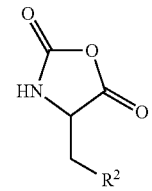
(III)

in the presence of a base
wherein
$R^2$ is a leaving group selected from halogen, $C_1$-$C_8$alkylsulfonyloxy, $C_1$-$C_8$haloalkylsulfonyloxy, $C_1$-$C_8$arylsulfonyloxy or $C_1$-$C_8$arylsulfonyloxy substituted by one to five $R^{11}$, or a phosphonate ester; and
each $R^{11}$ is independently $C_1$-$C_4$alkyl, $C_1$-$C_4$haloalkyl, $C_1$-$C_4$alkoxy, $C_1$-$C_4$haloalkoxy, cyano or halogen.

In one aspect the present invention relates to a process for the preparation of a compound of formula (I)

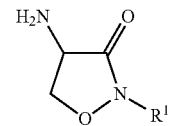
(I)

wherein
$R^1$ is $C_1$-$C_8$alkyl, $C_1$-$C_8$haloalkyl, aryl or aryl substituted by one to five $R^{11}$, or aryl-$C_1$-$C_4$alkylene or aryl-$C_1$-$C_4$alkylene substituted by one to five $R^{11}$; and
each $R^{11}$ is independently $C_1$-$C_4$alkyl, $C_1$-$C_4$haloalkyl, $C_1$-$C_4$alkoxy, $C_1$-$C_4$haloalkoxy, cyano or halogen;

comprising
a-1. reacting the compound of formula (II)

(II)

with the compound of formula (III)

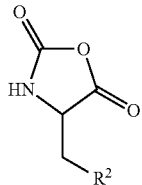
(III)

in the presence of a suitable acid
wherein
R² is a leaving group selected from halogen, $C_1$-$C_8$alkylsulfonyloxy, $C_1$-$C_8$haloalkylsulfonyloxy, $C_1$-$C_8$arylsulfonyloxy or $C_1$-$C_8$arylsulfonyloxy substituted by one to five $R^{11}$, or a phosphonate ester; and
each $R^{11}$ is independently $C_1$-$C_4$alkyl, $C_1$-$C_4$haloalkyl, $C_1$-$C_4$alkoxy, $C_1$-$C_4$haloalkoxy, cyano or halogen;
to produce the compound of formula (IV) or a salt thereof

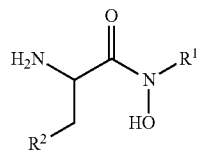
(IV)

wherein R¹ and R² are as defined for the compound of formula (I) and formula (III)
and
a-2. converting the compound of formula (IV) to the compound of formula (I) in the presence of a suitable base.

In one aspect the present invention relates to a process for the preparation of a compound of formula (IV)

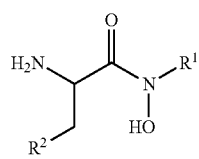
(IV)

comprising
a-1. reacting the compound of formula (II)

(II)

with the compound of formula (III)

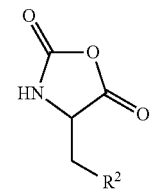
(III)

in the presence of a suitable acid
wherein
R¹ is $C_1$-$C_8$alkyl, $C_1$-$C_8$haloalkyl, aryl or aryl substituted by one to five $R^{11}$, or aryl-$C_1$-$C_4$alkylene or aryl-$C_1$-$C_4$alkylene substituted by one to five $R^{11}$;
R² is a leaving group selected from halogen, $C_1$-$C_8$alkylsulfonyloxy, $C_1$-$C_8$haloalkylsulfonyloxy, $C_1$-$C_8$arylsulfonyloxy or $C_1$-$C_8$arylsulfonyloxy substituted by one to five $R^{11}$, or a phosphonate ester; each $R^{11}$ is independently $C_1$-$C_4$alkyl, $C_1$-$C_4$haloalkyl, $C_1$-$C_4$alkoxy, $C_1$-$C_4$haloalkoxy, cyano or halogen.

In one aspect the present invention relates to a process for the preparation of a compound of formula (I)

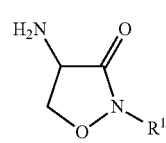
(I)

comprising the step a-2
a-2. converting the compound of formula (IV)

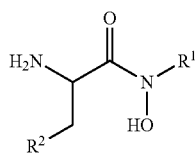
(IV)

to the compound of formula (I) in the presence of a suitable base
wherein
R¹ is $C_1$-$C_8$alkyl, $C_1$-$C_8$haloalkyl, aryl or aryl substituted by one to five $R^{11}$, or aryl-$C_1$-$C_4$alkylene or aryl-$C_1$-$C_4$alkylene substituted by one to five $R^{11}$;
R² is $C_1$-$C_8$alkylsulfonyloxy, $C_1$-$C_8$haloalkylsulfonyloxy, $C_1$-$C_8$arylsulfonyloxy or $C_1$-$C_8$arylsulfonyloxy substituted by one to five $R^{11}$, or a phosphonate ester; and
each $R^{11}$ is independently $C_1$-$C_4$alkyl, $C_1$-$C_4$haloalkyl, $C_1$-$C_4$alkoxy, $C_1$-$C_4$haloalkoxy, cyano or halogen.

In one aspect the present invention relates to a compound of formula (IV)

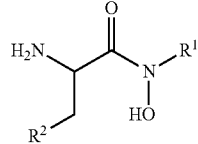
(IV)

wherein
$R^1$ is $C_1$-$C_8$alkyl, $C_1$-$C_8$haloalkyl, aryl or aryl substituted by one to five $R^{11}$, or aryl-$C_1$-$C_4$alkylene or aryl-$C_1$-$C_4$alkylene substituted by one to five $R^{11}$;
$R^2$ is $C_1$-$C_8$alkylsulfonyloxy, $C_1$-$C_8$haloalkylsulfonyloxy, $C_1$-$C_8$arylsulfonyloxy or $C_1$-$C_8$arylsulfonyloxy substituted by one to five $R^{11}$, or a phosphonate ester; and
each $R^{11}$ is independently $C_1$-$C_4$alkyl, $C_1$-$C_4$haloalkyl, $C_1$-$C_4$alkoxy, $C_1$-$C_4$haloalkoxy, cyano or halogen;
or a salt or N-oxide thereof.

In one aspect the present invention relates to a process for the preparation of a compound of formula (I)

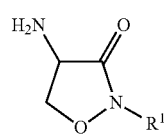
(I)

comprising
i. reacting a compound of formula (II) or a salt thereof

(II)

with a compound of formula (V)

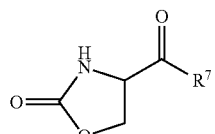
(V)

in the presence of a suitable base to produce a compound of formula (VI)

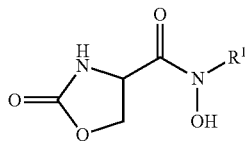
(VI)

and
ii. converting the compound of formula (VI) to a compound of formula (I) by treatment of the compound of formula (VI) with an aqueous base
wherein
$R^1$ is $C_1$-$C_8$alkyl, $C_1$-$C_8$haloalkyl, $C_3$-$C_6$ cycloalkyl, aryl or aryl substituted by one to five $R^{11}$, or aryl-$C_1$-$C_4$alkylene or aryl-$C_1$-$C_4$alkylene substituted by one to five $R^{11}$; and
each $R^{11}$ is independently $C_1$-$C_4$alkyl, $C_1$-$C_4$haloalkyl, $C_1$-$C_4$alkoxy, $C_1$-$C_4$haloalkoxy, cyano or halogen;
$R^7$ is hydroxy or halogen or OM where M is Na, K, Li.

In one aspect the present invention relates to a compound of formula (V)

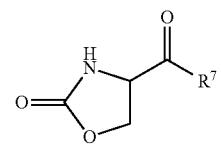
(V)

wherein $R^7$ is is OM where M is Na, K, Li.

A compound of formula (VI)

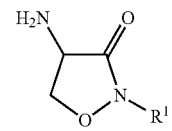
(VI)

wherein
$R^1$ is $C_1$-$C_8$alkyl, $C_1$-$C_8$haloalkyl, $C_3$-$C_6$ cycloalkyl, aryl or aryl substituted by one to five $R^{11}$, or aryl-$C_1$-$C_4$alkylene or aryl-$C_1$-$C_4$alkylene substituted by one to five $R^{11}$;
each $R^{11}$ is independently $C_1$-$C_4$alkyl, $C_1$-$C_4$haloalkyl, $C_1$-$C_4$alkoxy, $C_1$-$C_4$haloalkoxy, cyano or halogen;
or a salt or N-oxide thereof.

In one aspect the present invention relates to a compound of formula (I)

(I)

wherein $R^1$ is aryl or aryl substituted by one to five $R^{11}$;
each $R^{11}$ is independently $C_1$-$C_4$alkyl, $C_1$-$C_4$haloalkyl, $C_1$-$C_4$alkoxy, $C_1$-$C_4$haloalkoxy, cyano or halogen A process for the preparation of a compound of formula (V)

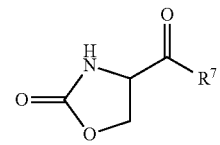
(V)

wherein $R^7$ is OM where M is Na, K, Li.

comprising the reaction of a compound (XV)

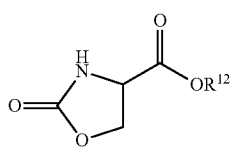
(XV)

where $R^{12}$ is $C_1$-$C_4$ alkyl
with an alkali metal salt MOH wherein M is Na, K, Li.

In one aspect the present invention relates to a process for the preparation of a compound of formula (V)

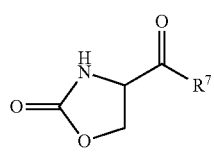
(V)

wherein $R^7$ is OM where M is Na, K, Li.
comprising the reaction of a compound (XVI)

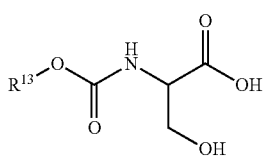
(XVI)

$R^{13}$ is $C_1$-$C_4$ alkyl, benzyl or phenyl
with an alkali metal salt MOH wherein M is Na, K, Li.

In the processes above the compounds of formula (I), (III) and (IV) are preferably compounds of formula (I*), (III*) and (IV*) or enriched mixtures thereof

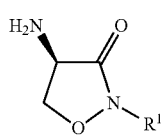
(I*)

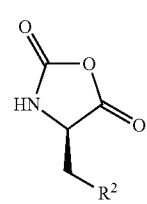
(III*)

(IV*)

wherein $R^1$ is as defined for the compound of formula (I) and $R^2$ is a leaving group, or a salt or N-oxide thereof.

In a further aspect the invention provides a compound of formula (IV)

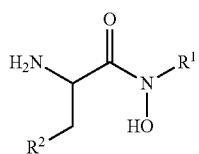
(IV)

wherein $R^1$ is as defined for the compound of formula (I) and $R^2$ is a leaving group as defined below, or a salt or N-oxide thereof.

Preferably the compound of formula (IV) is a compound of formula (IV*).

In a further aspect the invention provides a process for the preparation of a compound of formula (I)

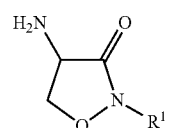
(I)

wherein
$R^1$ is $C_1$-$C_8$alkyl, $C_1$-$C_8$haloalkyl, $C_3$-$C_6$ cycloalkyl, aryl or aryl substituted by one to five $R^{11}$, or aryl-$C_1$-$C_4$alkylene or aryl-$C_1$-$C_4$alkylene substituted by one to five $R^{11}$; and
each $R^{11}$ is independently $C_1$-$C_4$alkyl, $C_1$-$C_4$haloalkyl, $C_1$-$C_4$alkoxy, $C_1$-$C_4$haloalkoxy, cyano or halogen;
comprising
i. reacting a compound of formula (II) or a salt thereof

(II)

wherein $R^1$ is as defined for the compound of formula (I) with a compound of formula (V)

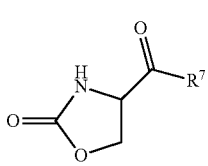
(V)

wherein $R^7$ is hydroxy or halogen or OM where M is Na, K, Li.

in the presence of a suitable base to produce a compound of formula (VI)

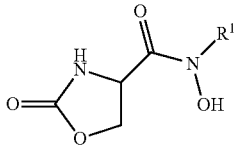

(VI)

wherein $R^1$ as defined for the compound of formula (I); and ii. converting the compound of formula (VI) to a compound of formula (I) by treatment of the compound of formula (VI) with an aqueous base.

Examples of suitable bases used in the step i and in the step ii and preferred bases used in the step i and in the step ii. are given below.

Preferably $R^1$ is $C_1$-$C_8$alkyl, $C_1$-$C_8$haloalkyl, aryl or aryl substituted by one to five $R^{11}$, or aryl-$C_1$-$C_4$alkylene or aryl-$C_1$-$C_4$alkylene substituted by one to five $R^{11}$; and each $R^{11}$ is independently $C_1$-$C_4$alkyl, $C_1$-$C_4$haloalkyl, $C_1$-$C_4$alkoxy, $C_1$-$C_4$haloalkoxy, cyano or halogen;

Preferably $R^7$ is hydroxy or halogen.

Equally preferred $R^1$ is $C_3$-$C_6$ cycloalkyl; and $R^7$ is OM where M is Na, K, Li.

In a further aspect the invention provides a process for the preparation of a compound of formula (VI) as defined in above, comprising performing step i. as defined above. In a further aspect the invention provides a process for the preparation of a compound of formula (I) as defined above, comprising performing step ii. as defined above.

In the processes above the compounds of formula (I), (V) and (VI) are preferably compounds of formula (I*), (V*) and (VI*) or enriched mixtures thereof:

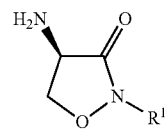

(I*)

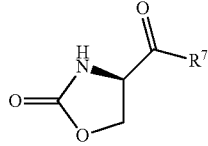

(V*)

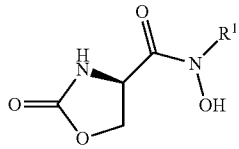

(VI*)

wherein $R^1$ is as defined for the compound of formula (I) and $R^7$ is as defined for the compound of formula (V).

In a further aspect the invention provides a compound of formula (VI)

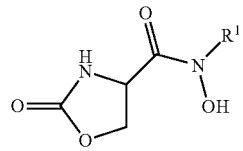

(VI)

wherein $R^1$ is as defined for the compound of formula (I) or a salt of N-oxide thereof. Preferably the compound of formula (VI) is a compound of formula (VI*).

In a further aspect the invention provides a compound of formula (V)

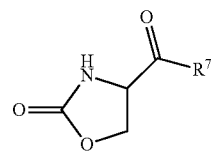

(V)

wherein $R^7$ is OLi, ONa or OK

In a further aspect the invention provides a compound of formula (I)

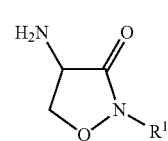

(I)

wherein $R^1$ is aryl or aryl substituted by one to five $R^{11}$.
each $R^{11}$ is independently $C_1$-$C_4$alkyl, $C_1$-$C_4$haloalkyl, $C_1$-$C_4$alkoxy, $C_1$-$C_4$haloalkoxy, cyano or halogen All aspects of the invention may also include further processing of the compound of formula (I). In particular, the process may include reacting the compound of formula (I) with a second compound, wherein the second compound comprises a carboxylic acid, acid halide, ester or thioester functional group, and the reaction comprises reacting the amine functional group of the compound of formula (I) with the carboxylic acid, acid halide, ester or thioester functional group of the second compound such that the compound of formula (I) is coupled to the second compound via an amide functional group, or wherein the second compound comprises a dicarbonate group, and the reaction comprises reacting the amine functional group of the compound of formula (I) with the dicarbonate group of the second compound, such that the compound of formula (I) is coupled to the second compound via a carbamate functional group.

In one embodiment the second compound is a compound of formula (XII)

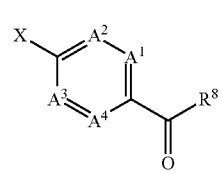

(XII)

wherein

X is a leaving group, cyano, formyl, acetyl, C(O)CH=C(R³)R⁴, C(O)CH₂C(OH)(R³)R⁴ or group A

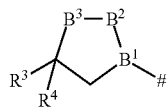

(A)

—B¹—B—B³— is —C=N—O—, —C=N—CH₂—, —C=CH—O— or —N—CH₂—CH₂—;

A¹, A², A³ and A⁴ are independently of one another C—H, C—R⁵, or nitrogen;

R³ is $C_1$-$C_8$haloalkyl;

R⁴ is aryl or aryl substituted by one to three R⁶, or R⁴ is heterocyclyl or heterocyclyl substituted by one to three R⁶;

each R⁵ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, $C_1$-$C_8$alkoxycarbonyl-, or two R⁵ on adjacent carbon atoms together form a —CH=CH—CH=CH— bridge or a —N=CH—CH=CH— bridge;

each R⁶ is independently halogen, cyano, nitro, $C_1$-$C_8$alkyl, $C_1$-$C_8$haloalkyl, $C_1$-$C_8$alkoxy, or $C_1$-$C_8$haloalkoxy;

R⁸ is hydroxy, $C_1$-$C_6$alkoxy or chloro, fluoro, bromo, or SR^x wherein R^x is H, $C_1$-$C_6$alkyl, imidazole or pyrrole; and each R¹¹ is independently $C_1$-$C_4$alkyl, $C_1$-$C_4$haloalkyl, $C_1$-$C_4$alkoxy, $C_1$-$C_4$haloalkoxy, cyano or halogen;

and the process results in a compound of formula (VIII)

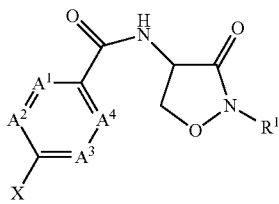

(VIII)

wherein A¹, A², A³, A⁴ and X are as defined for the compound of formula (XII) and R¹ is as defined for the compound of formula (I).

In another embodiment the second compound is a compound of formula (XIII)

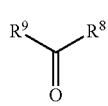

(XIII)

wherein R⁹ is hydrogen, $C_1$-$C_8$alkyl or $C_1$-$C_8$haloalkyl and R⁸ is as defined for compounds of formula (XII);

and the process results in a compound of formula (IX)

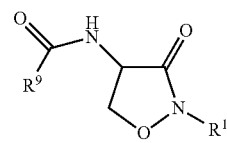

(IX)

wherein R¹ is as defined for the compound of formula (I) and R⁹ is as defined for the compound of formula (XIII).

In another embodiment the second compound is a compound of formula (XIVa) or (XIVb)

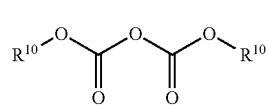

(XIVa)

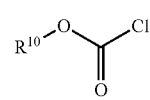

(XIVb)

wherein each R¹⁰ is independently $C_1$-$C_8$alkyl, $C_1$-$C_8$haloalkyl, aryl-$C_1$-$C_4$alkylene- or aryl-$C_1$-$C_4$alkylene- substituted by one to five R¹¹, wherein each R¹¹ is independently $C_1$-$C_4$alkyl, $C_1$-$C_4$haloalkyl, $C_1$-$C_4$alkoxy, $C_1$-$C_4$haloalkoxy, cyano or halogen;

and the process results in a compound of formula X

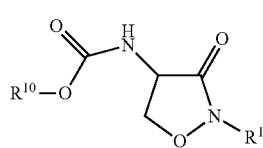

(X)

wherein R¹ is as defined for the compound of formula (I) and R¹⁰ is as defined for the compound of formula (XIVa) and XIVb.

In a further aspect the invention provides a process wherein the compound of formula (I) is reacted with a second compound, wherein the second compound comprises a carboxylic acid, acid halide, ester or thioester functional group, and the reaction comprises reacting the amine functional group of the compound of formula (I) with the carboxylic acid, acid halide, ester or thioester functional group of the second compound such that the compound of formula (I) is coupled to the second compound via an amide functional group, or wherein the second compound comprises a dicarbonate group, and the reaction comprises reacting the amine functional group of the compound of formula (I) with the dicarbonate group of the second compound, such that the compound of formula (I) is coupled to the second compound via a carbamate functional group. Preferably in the process wherein the compound of formula (I) is reacted with a second compound wherein
the second compound is a compound of formula (XII)

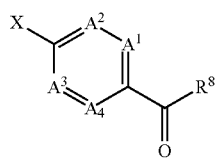
(XII)

and the process results in a compound of formula (VIII)

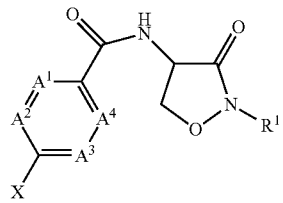
(VIII)

wherein
X is a leaving group selected from halogen, $C_1$-$C_8$alkylsulfonyloxy, $C_1$-$C_8$haloalkylsulfonyloxy, $C_1$-$C_8$arylsulfonyloxy or $C_1$-$C_8$arylsulfonyloxy substituted by one to five $R^{11}$, or a phosphonate ester, cyano, formyl, acetyl, C(O)CH=C($R^3$)$R^4$, C(O)CH$_2$C(OH)($R^3$)$R^4$ or group A

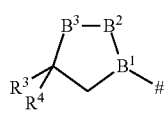
(A)

—$B^1$—$B^2$—$B^3$— is —C=N—O—, —C=N—CH$_2$—, —C=CH$_2$—O— or —N—CH$_2$—CH$_2$—;
$A^1$, $A^2$, $A^3$ and $A^4$ are independently of one another C—H, C—$R^5$, or nitrogen;
$R^3$ is $C_1$-$C_8$haloalkyl;
$R^4$ is aryl or aryl substituted by one to three $R^6$, or $R^4$ is heterocyclyl or heterocyclyl substituted by one to three $R^6$;
each $R^5$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, $C_1$-$C_8$alkoxycarbonyl-, or two $R^5$ on adjacent carbon atoms together form a —CH=CH—CH=CH— bridge or a —N=CH—CH=CH— bridge;
each $R^6$ is independently halogen, cyano, nitro, $C_1$-$C_8$alkyl, $C_1$-$C_8$haloalkyl, $C_1$-$C_8$alkoxy, or $C_1$-$C_8$haloalkoxy;
$R^8$ is hydroxy, $C_1$-$C_6$alkoxy, fluoro, chloro, bromo, or $SR^x$ wherein $R^x$ is H, $C_1$-$C_6$alkyl, imidazole or pyrrole; and
each $R^{11}$ is independently $C_1$-$C_4$alkyl, $C_1$-$C_4$haloalkyl, $C_1$-$C_4$alkoxy, $C_1$-$C_4$haloalkoxy, cyano or halogen;
$R^1$ is $C_1$-$C_8$alkyl, $C_1$-$C_8$haloalkyl, aryl or aryl substituted by one to five $R^{11}$, or aryl-$C_1$-$C_4$alkylene or aryl-$C_1$-$C_4$alkylene substituted by one to five $R^{11}$; and
each $R^{11}$ is independently $C_1$-$C_4$alkyl, $C_1$-$C_4$haloalkyl, $C_1$-$C_4$alkoxy, $C_1$-$C_4$haloalkoxy, cyano or halogen;

or
the second compound is a compound of formula (XIII)

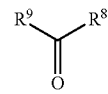
(XIII)

wherein and the process results in a compound of formula (IX)

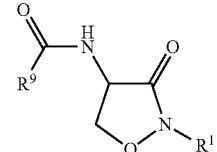
(IX)

wherein
$R^1$ is $C_1$-$C_8$alkyl, $C_1$-$C_8$haloalkyl, aryl or aryl substituted by one to five $R^{11}$, or aryl-$C_1$-$C_4$alkylene or aryl-$C_1$-$C_4$alkylene substituted by one to five $R^{11}$; and
$R^9$ is hydrogen, $C_1$-$C_8$alkyl or $C_1$-$C_8$haloalkyl and $R^8$ is as defined for compound of formula (XII);
each $R^{11}$ is independently $C_1$-$C_4$alkyl, $C_1$-$C_4$haloalkyl, $C_1$-$C_4$alkoxy, $C_1$-$C_4$haloalkoxy, cyano or halogen;
or
the second compound is a compound of formula (XIVa) or (XIVb)

$$R^{10}-O-\overset{O}{\underset{\parallel}{C}}-O-\overset{O}{\underset{\parallel}{C}}-O-R^{10}$$ (XIVa)

$$R^{10}-O-\overset{O}{\underset{\parallel}{C}}-Cl$$ (XIVb)

and the process results in a compound of formula X

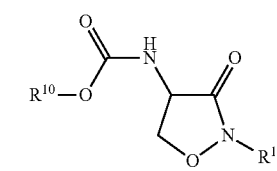
(X)

wherein
$R^1$ is $C_1$-$C_8$alkyl, $C_1$-$C_8$haloalkyl, aryl or aryl substituted by one to five $R^{11}$, or aryl-$C_1$-$C_4$alkylene or aryl-$C_1$-$C_4$alkylene substituted by one to five $R^{11}$;
each $R^{10}$ is independently $C_1$-$C_8$alkyl, $C_1$-$C_8$haloalkyl, aryl-$C_1$-$C_4$alkylene- or aryl-$C_1$-$C_4$alkylene-substituted by one to five $R^{11}$;
each $R^{11}$ is independently $C_1$-$C_4$alkyl, $C_1$-$C_4$haloalkyl, $C_1$-$C_4$alkoxy, $C_1$-$C_4$haloalkoxy, cyano or halogen;
In a further aspect the invention provides a process for the preparation of a compound of formula (VIII) or a salt or N-oxide thereof

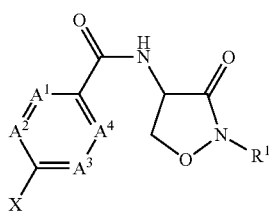

(VIII)

comprising the preparation of a compound of formula (I)

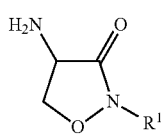

(I)

according to the process any one of claims 1 or 2 or 3 or 4 or 6, and reacting the compound of formula (I) with compound of formula (XII)

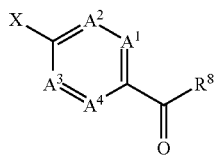

(XII)

wherein
X is a leaving group selected from halogen, $C_1$-$C_8$alkylsulfonyloxy, $C_1$-$C_8$haloalkylsulfonyloxy, $C_1$-$C_8$arylsulfonyloxy or $C_1$-$C_8$arylsulfonyloxy substituted by one to five $R^{11}$, or a phosphonate ester, cyano, formyl, acetyl, $C(O)CH=C(R^3)R^4$, $C(O)CH_2C(OH)(R^3)R^4$ or group A

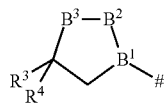

(A)

—$B^1$—$B^2$—$B^3$— is —C=N—O—, —C=N—$CH_2$—, —C=$CH_2$—O— or —N—$CH_2$—$CH_2$—;
$A^1$, $A^2$, $A^3$ and $A^4$ are independently of one another C—H, C—$R^5$, or nitrogen;
$R^3$ is $C_1$-$C_8$haloalkyl;
$R^4$ is aryl or aryl substituted by one to three $R^6$, or $R^4$ is heterocyclyl or heterocyclyl substituted by one to three $R^6$;
each $R^5$ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, $C_1$-$C_8$alkoxycarbonyl-, or two $R^5$ on adjacent carbon atoms together form a —CH=CH—CH=CH— bridge or a —N=CH—CH=CH— bridge;
each $R^6$ is independently halogen, cyano, nitro, $C_1$-$C_8$alkyl, $C_1$-$C_8$haloalkyl, $C_1$-$C_8$alkoxy, or $C_1$-$C_8$haloalkoxy;

$R^8$ is hydroxy, $C_1$-$C_6$alkoxy, chloro, cluoro, bromo, or $SR^x$ wherein $R^x$ is H, $C_1$-$C_6$alkyl, imidazole or pyrrole;
$R^1$ is $C_1$-$C_8$alkyl, $C_1$-$C_8$haloalkyl, aryl or aryl substituted by one to five $R^{11}$, or aryl-$C_1$-$C_4$alkylene or aryl-$C_1$-$C_4$alkylene substituted by one to five $R^{11}$; and
each $R^{11}$ is independently $C_1$-$C_4$alkyl, $C_1$-$C_4$haloalkyl, $C_1$-$C_4$alkoxy, $C_1$-$C_4$haloalkoxy, cyano or halogen.

The compounds of the invention may exist in different geometric or optical isomers or tautomeric forms. In particular, the compounds of the invention may contain one or more asymmetric carbon atoms and may exist as enantiomers (or as pairs of diastereoisomers) or as mixtures of such. This invention covers all such isomers and tautomers and mixtures thereof in all proportions as well as isotopic forms such as deuterated compounds. The compounds and processes of the invention include N-oxides and salts where possible.

Alkyl groups (either alone or as part of a larger group, such as alkoxy-, alkylthio-, alkylsulfinyl-, alkylsulfonyl-, alkylcarbonyl- or alkoxycarbonyl-) can be in the form of a straight or branched chain and are, for example, methyl, ethyl, propyl, prop-2-yl, butyl, but-2-yl, 2-methyl-prop-1-yl or 2-methyl-prop-2-yl. The alkyl groups are preferably $C_1$-$C_6$, more preferably $C_1$-$C_4$, most preferably $C_1$-$C_3$ alkyl groups. Where an alkyl moiety is said to be substituted, the alkyl moiety is preferably substituted by one to four substituents, most preferably by one to three substituents.

Alkylene groups can be in the form of a straight or branched chain and are, for example, —$CH_2$—, —$CH_2$—$CH_2$—, —$CH(CH_3)$—, —$CH_2$—$CH_2$—$CH_2$—, —$CH(CH_3)$—$CH_2$—, or —$CH(CH_2CH_3)$—. The alkylene groups are preferably $C_1$-$C_3$, more preferably $C_1$-$C_2$, most preferably $C_1$ alkylene groups. Where an alkylene moiety is said to be substituted, the alkyl moiety is preferably substituted by one to four substituents, most preferably by one to three substituents.

Alkenyl groups can be in the form of straight or branched chains, and can be, where appropriate, of either the (E)- or (Z)-configuration. Examples are vinyl and allyl. The alkenyl groups are preferably $C_2$-$C_6$, more preferably $C_2$-$C_4$, most preferably $C_2$-$C_3$ alkenyl groups. Where an alkenyl moiety is said to be substituted, the alkyl moiety is preferably substituted by one to four substituents, most preferably by one to three substituents.

Alkynyl groups can be in the form of straight or branched chains. Examples are ethynyl and propargyl. The alkynyl groups are preferably $C_2$-$C_6$, more preferably $C_2$-$C_4$, most preferably $C_2$-$C_3$ alkynyl groups. Where an alkynyl moiety is said to be substituted, the alkyl moiety is preferably substituted by one to four substituents, most preferably by one to three substituents.

Halogen is fluorine, chlorine, bromine or iodine.

Haloalkyl groups (either alone or as part of a larger group, such as haloalkoxy-, haloalkylthio-, haloalkylsulfinyl- or haloalkylsulfonyl-) are alkyl groups which are substituted by one or more of the same or different halogen atoms and are, for example, difluoromethyl, trifluoromethyl, chlorodifluoromethyl or 2,2,2-trifluoro-ethyl.

Haloalkenyl groups are alkenyl groups which are substituted by one or more of the same or different halogen atoms and are, for example, 2,2-difluoro-vinyl or 1,2-dichloro-2-fluoro-vinyl.

Haloalkynyl groups are alkynyl groups which are substituted by one or more of the same or different halogen atoms and are, for example, 1-chloro-prop-2-ynyl.

Cycloalkyl groups or carbocyclic rings can be in mono- or bi-cyclic form and are, for example, cyclopropyl, cyclobutyl, cyclohexyl and bicyclo[2.2.1]heptan-2-yl. The cycloalkyl groups are preferably $C_3$-$C_8$, more preferably $C_3$-$C_6$ cycloalkyl groups. Where a cycloalkyl moiety is said to be substituted, the cycloalkyl moiety is preferably substituted by one to four substituents, most preferably by one to three substituents.

Aryl groups (either alone or as part of a larger group, such as aryl-alkylene-) are aromatic ring systems which can be in mono-, bi- or tricyclic form. Examples of such rings include phenyl, naphthyl, anthracenyl, indenyl or phenanthrenyl. Preferred aryl groups are phenyl and naphthyl, phenyl being most preferred. Where an aryl moiety is said to be substituted, the aryl moiety is preferably substituted by one to four substituents, most preferably by one to three substituents.

Heteroaryl groups (either alone or as part of a larger group, such as heteroaryl-alkylene-) are aromatic ring systems containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl (e.g. 1.2.4 triazoyl), furanyl, thiophenyl, oxazolyl, isoxazolyl, oxadiazolyl, thiazolyl, isothiazolyl, tetrazolyl and thiadiazolyl. Examples of bicyclic groups include purinyl, quinolinyl, cinnolinyl, quinoxalinyl, indolyl, indazolyl, benzimidazolyl, benzothiophenyl and benzothiazolyl. Monocyclic heteroaryl groups are preferred, pyridyl being most preferred. Where a heteroaryl moiety is said to be substituted, the heteroaryl moiety is preferably substituted by one to four substituents, most preferably by one to three substituents.

Heterocyclyl groups or heterocyclic rings (either alone or as part of a larger group, such as heterocyclyl-alkylene-) are defined to include heteroaryl groups and in addition their unsaturated or partially unsaturated analogues. Examples of monocyclic groups include isoxazolyl, thietanyl, pyrrolidinyl, dihydrofuranyl, tetrahydrofuranyl, dihydropyranyl, tetrahydropyranyl, dihydrothiophene, [1,3]dioxolanyl, piperidinyl, piperazinyl, [1,4]dioxanyl, morpholinyl, thiophene, oxetanyl, tetrahydropyranyl, 3-oxo-isoxazolidinyl-, 2,5-dioxo-1-pyrrolidinyl-, 2-oxo-1-pyrrolidinyl-, 4-oxo-1,3-oxazinanyl, 1-oxa-3,4-diazolyl, including their oxidised versions such as 1-oxo-thietanyl and 1,1-dioxo-thietanyl, thiophene 1-oxide, thiophene 1,1-dioxide, dihydrothiophene, dihydrothiophene 1-oxide, or dihydrothiophene 1,1-dioxide. Examples of bicyclic groups include 2,3-dihydrobenzofuranyl, benzo[1,4]dioxolanyl, benzo[1,3]dioxolanyl, chromenyl, and 2,3-dihydro-benzo[1,4]dioxinyl. Where a heterocyclyl moiety is said to be substituted, the heterocyclyl moiety is preferably substituted by one to four substituents, most preferably by one to three substituents. Heterocyclyl groups (and heteroaryl groups) according to the present invention do not contain adjacent oxygen atoms, adjacent sulphur atoms, or adjacent sulphur and oxygen atoms. Preferred heterocyclyl groups are thiophene, thiophene 1-oxide, thiophene 1,1-dioxide, dihydrothiophene, dihydrothiophene 1-oxide, dihydrothiophene 1,1-dioxide, pyridyl, pyrazinyl, pyrimidinyl, pyrrolyl, imidazolyl, pyrazolyl, triazolyl, and tetrazoyl, Leaving groups according to the invention include halogen, $C_1$-$C_8$alkylsulfonyloxy, $C_1$-$C_8$haloalkylsulfonyloxy, $C_1$-$C_8$arylsulfonyloxy or $C_1$-$C_8$arylsulfonyloxy substituted by one to five $R^{11}$, wherein each $R^{11}$ is independently $C_1$-$C_4$alkyl, $C_1$-$C_4$haloalkyl, $C_1$-$C_4$alkoxy, $C_1$-$C_4$haloalkoxy, cyano or halogen (aryl is preferably phenyl), and phosphonate esters (e.g. —OP(O)(OR)$_2$, wherein R is methyl or ethyl). A preferred leaving group is halogen, in particular chloro or bromo.

Preferred definitions are, in any combination, as set out below.

Preferably $A^1$ is C—$R^5$.

Preferably $A^2$, $A^3$, $A^4$ are each CH.

Preferably —$B^1$—$B^2$—$B^3$— is —C=N—O—.

Preferably $R^1$ is $C_1$-$C_8$alkyl, $C_1$-$C_8$haloalkyl, more preferably ethyl or trifluoroethyl, even more preferably ethyl or 2,2,2-trifluoroethyl.

Preferably $R^2$ is chloro or bromo, more preferably chloro.

Preferably $R^3$ is trifluoromethyl, difluoromethyl or chlorodifluoromethyl, most preferably trifluoromethyl.

Preferably $R^4$ is group (B)

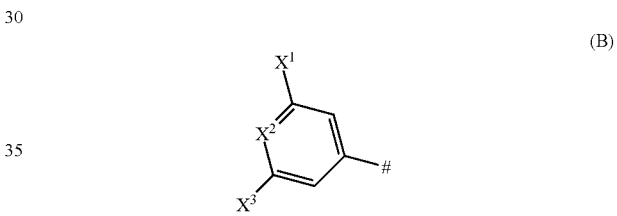

(B)

wherein $X^2$ is C—$X^4$ or nitrogen (preferably C—$X^4$); $X^1$, $X^3$ and $X^4$ are independently hydrogen, halogen or trihalomethyl, e.g. wherein at least two of $X^1$, $X^3$ and $X^4$ are not hydrogen.

Preferably $R^4$ is 3,5-dichlorophenyl, 3-chloro-4-fluorophenyl, 3-fluoro-4-chlorophenyl, 3,4-dichlorophenyl, 3-chloro-4-bromophenyl, 3,5-dichloro-4-fluorophenyl, 3,4,5-trichlorophenyl, 3,5-dichloro-4-iodophenyl, 3,4,5-trifluorophenyl, 3-chloro-5-bromophenyl, 3-chloro-5-fluorophenyl, 3-chloro-5-(trifluoromethyl)phenyl, 3-bromo-5-(trifluoromethyl)phenyl, 3,4-dichloro-5-(trifluoromethyl)phenyl, 3,5-bis(trifluoromethyl)phenyl, 4-chloro-3,5-bis(trifluoromethyl)phenyl, 3-(trifluoromethyl)phenyl, 2,6-dichloro-4-pyridyl, 2,6-bis(trifluoromethyl)-4-pyridyl, 2-chloro-4-pyridyl-, 2-trifluoromethyl-4-pyridyl, more preferably 3,5-dichloro-phenyl, 3-chloro-5-bromophenyl, 3-chloro-5-(trifluoromethyl)phenyl, 3,5-dichloro-4-fluorophenyl, 3,4,5-trichlorophenyl, 3,5-bis(trifluoromethyl)phenyl, 3-(trifluoromethyl)phenyl, 2,6-dichloro-4-pyridyl, 2,6-bis(trifluoromethyl)-4-pyridyl, 3,5-dichloro-4-bromophenyl, 3-bromo-5-(trifluoromethyl)phenyl, 3,5-dibromophenyl, or 3,4-dichlorophenyl, 2-chloro-4-pyridyl-, 2-trifluoromethyl-4-pyridyl, even more preferably 3,5-dichloro-phenyl, 3,5-dichloro-4-fluorophenyl, 3,4,5-trichlorophenyl, 3-(trifluoromethyl)phenyl, 3,5-bis(trifluoromethyl) phenyl, most preferably 3,5-dichloro-phenyl, 3,5-dichloro- 4-fluorophenyl, or 3,4,5-trichlorophenyl-. In one group of compounds $R^4$ is 3,5-dichloro-phenyl. In one group of compounds $R^4$ is 3,5-dichloro-4-fluorophenyl-. In one group of compounds $R^4$ is 3,4,5-trichlorophenyl-. In one group of compounds $R^4$ is 3,5-bis(trifluoromethyl)phenyl.

Preferably each $R^5$ is independently halogen, cyano, methyl, halomethyl, methoxy or halomethoxy, more preferably chloro, fluoro, cyano or methyl.

Preferably each $R^6$ is independently halogen, $C_1$-$C_8$alkyl, $C_1$-$C_8$haloalkyl, $C_1$-$C_8$alkoxy, $C_1$-$C_8$haloalkoxy, $C_1$-$C_8$alkylthio, or $C_1$-$C_8$haloalkylthio, more preferably bromo, chloro, fluoro, trifluoromethyl, methoxy, or methylthio, most preferably trifluoromethyl, fluoro or chloro.

Preferably $R^7$ is hydroxy, ONa, OLi, OK, chloro or bromo, more preferably, ONa, OLi or chloro.

Preferably $R^8$ is hydroxy, chloro or bromo, more preferably chloro.

Preferably $R^9$ is hydrogen or $C_1$-$C_6$alkyl, more preferably methyl.

Preferably each $R^{10}$ is independently $C_1$-$C_6$alkyl, more preferably $C_1$-$C_4$alkyl, most preferably t-butyl.

In one preferred embodiment the compounds of formula (I), (II) and (III) and (IV) are compounds wherein $R^1$ is ethyl or trifluoroethyl (preferably 2,2,2-trifluoroethyl) and $R^2$ is chloro or bromo, preferably chloro.

In a further preferred embodiment the compound of formula (IV) is a compound wherein $R^1$ is ethyl or trifluoroethyl (preferably 2,2,2-trifluoroethyl) and $R^2$ is chloro or bromo, preferably chloro.

In a further preferred embodiment the compounds of formula (I), (II), (V) and (VI) are compounds wherein $R^1$ is ethyl or trifluoroethyl (preferably 2,2,2-trifluoroethyl) and $R^7$ is hydroxy, ONa, OLi or chloro.

In a further preferred embodiment the compounds of formula (I), (II) and (VI) are compounds wherein $R^1$ is ethyl, trifluoroethyl or phenyl.

In a further preferred embodiment the compounds of formula (VI) is a compound wherein $R^1$ is ethyl or trifluoroethyl (preferably 2,2,2-trifluoroethyl)

In a further preferred embodiment the compounds of formula (VIII) and (XII) are compounds wherein $A^1$ is C—$R^5$;

$A^2$, $A^3$, $A^4$ are each CH;

$R^3$ is trifluoromethyl, difluoromethyl or chlorodifluoromethyl;

X is chloro, bromo, cyano, formyl, acetyl, C(O)CH=C($R^3$)$R^4$, C(O)CH$_2$C(OH)($R^3$)$R^4$ or group (A) as defined above;

$R^4$ is group (B) as defined above;

$X^2$ is C—$X^4$ or nitrogen (preferably C—$X^4$); $X^1$, $X^3$ and $X^4$ are independently hydrogen, halogen or trihalomethyl;

each $R^5$ is independently halogen, cyano, methyl, halomethyl, methoxy or halomethoxy, more preferably chloro, fluoro, cyano or methyl.

In a further preferred embodiment the compounds of formula (VIII) and (XII) are compounds wherein X is acetyl, C(O)CH=C($R^3$)$R^4$, C(O)CH$_2$C(OH)($R^3$)$R^4$ or group (A);

$A^1$ is C—$R^5$;

$A^2$, $A^3$, $A^4$ are each CH;

X is group (A)

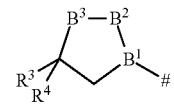

(A)

—$B^1$—$B^2$—$B^3$— is —C=N—O—, —C=N—CH$_2$—, —C=CH—O— or —N—CH$_2$—CH$_2$—, preferably —C=N—O—; $R^1$ is $C_1$-$C_8$alkyl, $C_1$-$C_8$haloalkyl, aryl or aryl substituted by one to five $R^{11}$, or aryl-$C_1$-$C_4$alkylene or aryl-$C_1$-$C_4$alkylene substituted by one to five $R^{11}$;

$R^3$ is trifluoromethyl, difluoromethyl or chlorodifluoromethyl;

$R^4$ is group (B)

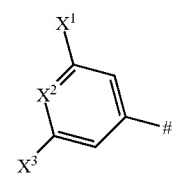

(B)

wherein $X^2$ is C—$X^4$ or nitrogen, $X^1$, $X^3$ and $X^4$ are independently hydrogen, halogen or trihalomethyl, $R^5$ is halogen, cyano, methyl, halomethyl, methoxy or halomethoxy;

each $R^{11}$ is independently $C_1$-$C_4$alkyl, $C_1$-$C_4$haloalkyl, $C_1$-$C_4$alkoxy, $C_1$-$C_4$haloalkoxy, cyano or halogen.

In one preferred embodiment the compounds of formula (IX) and (XIII) are compounds wherein $R^9$ is $C_1$-$C_6$alkyl.

In one preferred embodiment the compounds of formula (X) and (XIV) are compounds wherein each $R^{10}$ is $C_1$-$C_6$alkyl, preferably t-butyl.

In enriched mixtures of the invention, the molar proportion of the compound of formula (I*), (III*), (IV*), (V*), and/or (VI*) in the mixture is for example greater than 50%, e.g. at least 60, 70, 80, 90 or at least 95% of the total molar amount of the pair of enantiomers.

The following schemes describe the reactions of the invention in more detail. The substituent definitions are the same as defined above.

Scheme 1

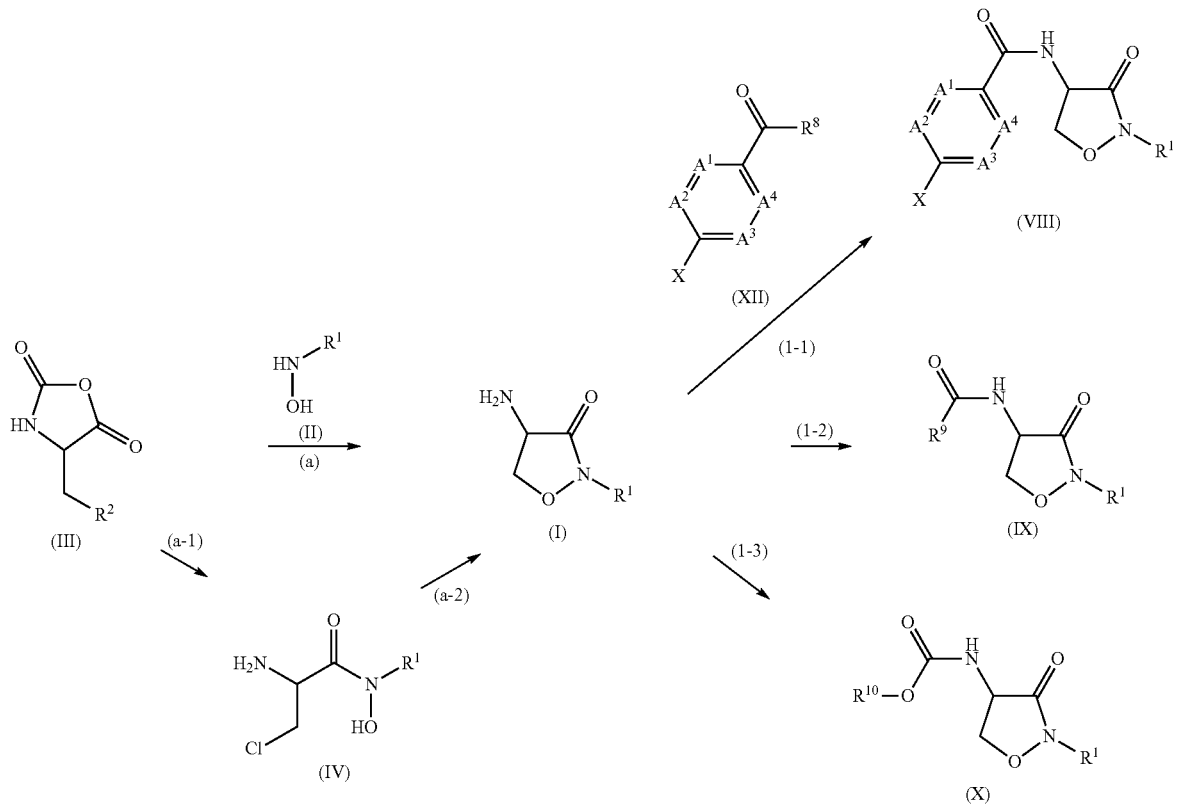

Step a

Compounds of formula (I) can be prepared by reacting a compound of formula (III) with a compound of formula (II) or salt thereof. Suitable salts of compounds of formula (II) include, but are not limited to halides, organic acids, and sulphur based salts, e.g. chloride, oxalate, sulfate, trifluoroacetate, mesylate and bromide.

The reactions of compounds of formula (III) and II are preferably carried out in the presence of a suitable base. Suitable bases include, but are not limited to nitrogen-based organic bases such as amines, pyridines and derivatives thereof, e.g. triethylamine, tri-n-propylamine, pyridine and diisopropylethylamine.

The reactions of compounds of III and II are preferably carried out in the presence of a solvent. Suitable solvents include, but are not limited to organic solvents, e.g. halogenated organic solvents or alcohols such as chloroform, dichloromethane, dichloroethane, monochlorobenzene, dichlorobenzene, trichlorobenzene, 4-fluorotoluene, methanol, ethanol, isopropanol, t-butanol, cyclohexanol, heptanol, octanol, or longer chain alcohols, and diethyleneglycol, preferably chloroform, dichloromethane, isopropyl alcohol and ethanol. It is also possible to conduct the reaction in a mixture of an organic solvent and water.

The reaction can be carried out at a temperature from −20° C. to 100° C., preferably from 0° C. to 30° C. (e.g. no lower than −20° C., preferably no lower than 0° C., e.g. no more than 100° C., preferably no more than 30° C.).

The reactions of compounds of formula (III) and II are preferably carried out in the presence of a catalyst. Suitable catalysts include, but are not limited to nucleophilic catalysts capable of promoting acyl transfer reactions such as 4-dialkylaminopyridines, N-alkylimidazoles, phosphines, imidazolylidene carbenes, 1,2-diamines, bicyclic amidines, isothioureas and guanidines, triazoles, suitable alcohols, iodide and cyanide salts, preferably 4-dimethylaminopyridine.

Step a-1

Compounds of formula (IV) can be prepared by reacting a compound of formula (III) with a compound of formula (II) or salt thereof as described under step a.

The reaction is preferably carried out in the presence of a solvent. Suitable solvents include, but are not limited to polar organic solvents, e.g. acetic acid, propanoic acid or longer chain carboxylic acids, trifluoroacetic acid, methanol, ethanol, isopropanol, t-butanol, cyclohenxanol, heptanol, octanol, or longer chain alcohols, trifluoroethanol, ethyleneglycol, acetonitrile and propionitrile, preferably acetic acid. It is also possible to conduct the reaction in a mixture of organic solvents or in a mixture of organic solvents and water.

The reaction is preferably carried out in the presence of a suitable acid. Suitable acids include, but are not limited to organic acids, e.g acetic acid, propanoic acid or longer chain carboxylic acids, trifluoroacetic acid. A preferred acid is acetic acid.

The reaction can be carried out at a temperature from −20° C. to 100° C., preferably from 0° C. to 30° C. (e.g. no lower than −20° C., preferably no lower than 0° C., e.g. no more than 100° C., preferably no more than 30° C.).

Depending on the conditions used, it may be advantageous to isolate compound IV as the corresponding salt. The salt may be formed with an acid already present in the reaction mixture or formed by adding an additional acid to the reaction mixture. Suitable acids include mineral acids and organic acids such as HCl, HBr, $H_2SO_4$, acetic acid and trifluoroacetic acid.

Step a-2

Compounds of formula (I) can be prepared by treating a compound of formula (IV) or a salt thereof as described under step a-1 with a base. Suitable bases include carbonates, hydroxides, nitrogen-based organic bases such as amines, pyridines and derivatives thereof, e.g. $Na_2CO_3$, $K_2CO_3$, $NaHCO_3$, NaOH, triethylamine, pyridine and diisopropylethylamine.

The reaction is preferably carried out in the presence of a solvent. Suitable solvents include, but are not limited to organic solvents such as diethylether, 1,2-dimethoxyethane, diethoxymethane, diglyme, t-butyl methyl ether, THF, 2-methyl-THF, dioxane; halogenated solvents such as chloroform, dichloromethane, dichloroethane, monochlorobenzene, dichlorobenzene, trichlorobenzene, 4-fluorotoluene; esters and ketones such as ethyl acetate, acetone 2-butanone, methylisobutylketone; ethers such as anisole, polar aprotic solvents such as acetonitrile, dimethylsulfoxide, dimethylformamide, N-methylpyrrolidone, dimethylacetamide; and alcohols, such as methanol, ethanol, isopropanol, t-BuOH, cyclohexanol, heptanol, octanol, or longer chain alcohols, and diethyleneglycol. Preferred organic solvents include tetrahydrofuran, dioxane and acetonitrile.

The reaction can be carried out at a temperature from $-20°$ C. to $100°$ C., preferably from $0°$ C. to $30°$ C.

Compounds of formula (I) can be isolated in a free form or as salts formed by adding an acid to compounds of formula (I) in a free base form. Suitable acids include mineral acids and organic acids such as HCl, HBr, $H_2SO_4$, acetic acid and trifluoroacetic acid.

When compounds of formula (II) and formula (III) are reacted under acidic conditions as described for step a-1 a compound of formula (IV) is isolated. Treating the compound of formula (IV) in a compound under basic conditions as described for step a-2 a compound of formula (I) is formed.

When compounds of formula (II) and formula (III) are reacted under basic conditions as described for step a intermediate compound of formula (IV) cannot be isolated and compound of formula (I) is formed directly.

Steps 1-1, 1-2 and 1-3

This is described under scheme 3 below. Steps a and 1-1, 1-2 and 1-3 can be conducted in the same reaction vessel (one-pot reaction) without isolation of the compound of formula (I), e.g. when the solvent is chloroform. In other words, compounds of formula (VIII), (IX) and (X) can be prepared from the compound of formula (III) without isolation of the compound of formula (I) or (IV). Alternatively, steps a-2 and 1-1, 1-2 and 1-3 can be conducted in the same reaction vessel (one-pot reaction) without isolation of the compound of formula (I).

Scheme 2

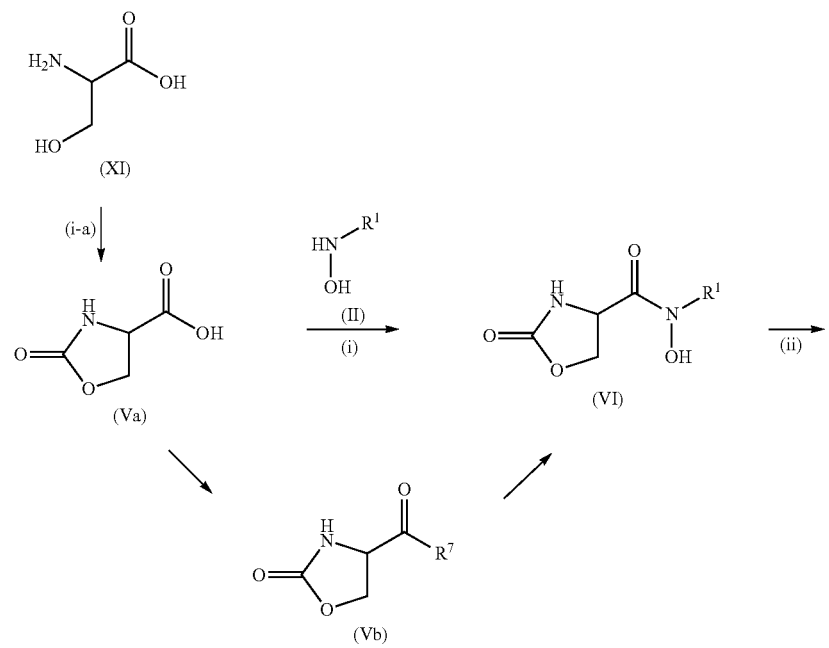

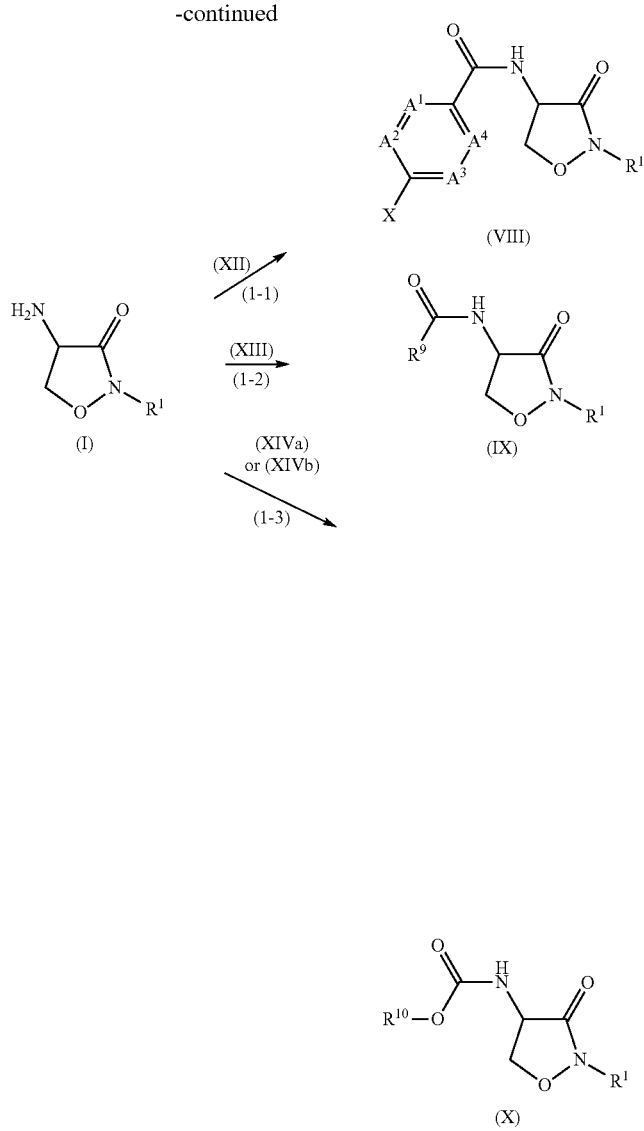

Step i-a

Compounds of formula (Va) can be prepared from compounds of formula (XI) by treatment with by phosgene or a derivative thereof e.g. diphosgene, triphosgene, ethyl chloroformate, benzylchloroformate, in the presence of aqueous base following the similar procedure described in Synthetic Comm. 1993, 23, 2839, which is incorporated herein by reference.

Step i

Compounds of formula (VI) can be prepared by reacting a compound of formula (Va) with a compound of formula (II). Preferably the reaction includes preparing the corresponding acid halide (preferably acid chloride) of the compound of formula (Va), compound (Vb), wherein $R^7$ is halogen, to facilitate the conversion to the compound of formula (VI). The acid halide, compound (Vb), wherein $R^7$ is halogen, can be prepared from the compound of formula (Va) under conditions well known to the person skilled in the art, such as by treatment with thionyl chloride, oxalyl chloride, phosgene, diphosgene or triphosgene.

Alternatively compound (Vb), wherein $R^7$ is halogen, can be prepared from an alkali metal (Li, Na, K) salt of compound of formula (Va), compound (Vc), by treatment with oxalyl chloride, thionyl chloride, phosgene, diphosgene or triphosgene in the presence of a phase transfer catalyst. Suitable phase transfer catalysts include, but are not limited to tetrabutylammonium chloride, tetrabutylammonium bromide, triethylbenzylammonium chloride, Aliquat® 336 and (1-hexadecyl)trimethylammonium bromide Scheme 2a

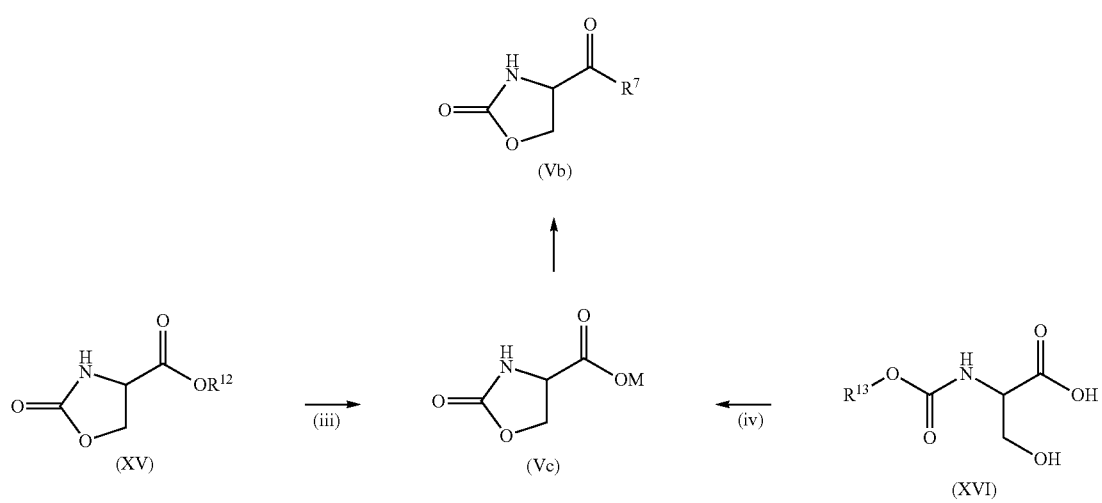

Alkali metal salts of compound of formula (V) where M is Li, Na or K, compounds Vc, can be prepared as shown in Scheme 2a.

Step iii and iv

Compounds of formula (Vc) where M is Li, Na or K can be prepared either by treating compounds of formula (XV) where $R^{12}$ is $C_1$-$C_4$ alkyl with LiOH, NaOH or KOH or by treating compounds of formula (XVI) where $R^{13}$ is $C_1$-$C_4$ alkyl, benzyl or phenyl with LiOH, NaOH or KOH. Suitable solvents include but are not limited to alcohols such as ethanol, methanol and isopropanol; polar organic solvents such as acetonitrile, dioxane, THF, 2-methyl-THF as well as water. Preferred solvents are ethanol and acetonitrile.

The reaction of the acid halide of compound of formula (V), compound (Vb), wherein $R^7$ is halogen, with compounds of formula (II) are preferably carried out in the presence of a base. Suitable bases include, but are not limited to carbonates, hydroxides, nitrogen-based organic bases such as amines, pyridines and derivatives thereof, e.g. triethylamine, tri-n-propylamine, pyridine, diisopropylethylamine, $Na_2CO_3$, $NaHCO_3$, NaOH and N-methyl morpholine.

The reaction of the acid halide of compound of formula (V), compound Vb, wherein $R^7$ is halogen, with compounds of formula (II) are optionally carried out in the presence of a nucleophilic catalyst. Suitable catalysts include, but are not limited to nucleophilic catalysts such as 4-dimethylaminopyridine.

Suitable solvents include, but are not limited to ethers, such as diethylether, 1,2-dimethoxyethane, diethoxymethane, diglyme, t-butyl methyl ether, THF, 2-methyl-THF, dioxane; halogenated solvents such as chloroform, dichloromethane, dichloroethane, monochlorobenzene, dichlorobenzene, trichlorobenzene, 4-fluorotoluene; esters and ketones such as ethyl acetate, acetone, 2-butanone, methylisobutylketone; anisole, polar aprotic solvents such as acetonitrile, dimethylsulfoxide, dimethylformamide, N-methylpyrrolidone and dimethylacetamide; or water/biphasic systems (as is known in the so-called Schotten-Baumann conditions) as well as hydrocarbons, such as toluene and xylenes both as pure isomers and a mixture of isomers.

Compounds of formula (II) can be used as such or in the form of their salts with acids, for example HCl, HBr, trifluoroacetic acid, oxalic acid, sulfuric acids and methanesulfonic acid.

The reaction can be carried out at a temperature from −20° C. to 100° C., preferably from −10° C. to 30° C., in particular between −5° C. to +10° C.; More preferably the reaction can be carried out at a temperature from 0° C. to +10° C.

Alternatively, it is possible to conduct the reaction in a biphasic system comprising an organic solvent, preferably ethyl acetate, 2-methyltetrahydrofuran, or dichloromethane, and an aqueous solvent, preferably a solution of sodium hydrogen carbonate or sodium carbonate or organic amine such as triethylamine or diisopropylethylamine.

Alternatively the reaction of the compound of formula (V) with the compound of formula (II) can be carried out in the presence of a coupling reagent, such as N,N'-dicyclohexylcarbodiimide ("DCC"), 1-ethyl-3-(3-dimethylamino-propyl)carbodiimide hydrochloride ("EDC") or bis(2-oxo-3-oxazolidinyl)phosphonic chloride ("BOP-Cl"), in the presence of a base, and optionally in the presence of a nucleophilic catalyst, such as hydroxybenzotriazole ("HOBT").

Suitable bases include carbonates, hydroxides, nitrogen-based organic bases such as amines, pyridines and derivatives thereof, e.g. $Na_2CO_3$, $K_2CO_3$, $NaHCO_3$, NaOH, triethylamine, pyridine, N-methyl morpholine and diisopropylethylamine.

Examples of suitable solvents include ethers, such as diethylether, 1,2-dimethoxyethane, diethoxymethane, diglyme, t-butyl methyl ether, THF, 2-methyl-THF, dioxane; halogenated solvents such as chloroform, dichloromethane, dichloroethane, monochlorobenzene, dichlorobenzene, trichlorobenzene, 4-fluorotoluene; esters and ketones such as ethyl acetate, acetone, 2-butanone, methylisobutylketone; anisole, polar aprotic solvents such as acetonitrile, dimethylsulfoxide, dimethylformamide, N-methylpyrrolidone, dimethylacetamide, hydrocarbons such as toluene and xylenes both as pure isomers and as a mixture of isomers. Preferred solvents are dichloromethane, dichloroethane, ethyl acetate, THF, 2-methyl-THF or dioxane.

The reaction can be carried out at a temperature from −20° C. to 100° C., preferably from −10° C. to 30° C., in particular from −5° C. to +5° C., more preferably from 0° C. to +5° C.

Step ii

Compounds of formula (I) can be prepared by treating compounds of formula (VI) with a base. Suitable bases include carbonates, hydroxides, nitrogen-based organic bases such as amines, pyridines and derivatives thereof, e.g. $Na_2CO_3$, $K_2CO_3$, $NaHCO_3$, NaOH, triethylamine, pyridine, N-methyl morpholine and diisopropylethylamine.

It is possible to conduct the reaction in a mixture of an organic solvent with water or in water alone. Preferably the reaction includes the presence of water.

Examples of organic solvents include ethers, such as diethylether, 1,2-dimethoxyethane, diethoxymethane, diglyme, t-butyl methyl ether, THF, 2-methyl-THF, dioxane; halogenated solvents such as chloroform, dichloromethane, dichloroethane, monochlorobenzene, dichlorobenzene, trichlorobenzene, 4-fluorotoluene; esters and ketones such as ethyl acetate, acetone 2-butanone, methylisobutylketone; anisole, polar aprotic solvents such as acetonitrile, dimethylsulfoxide, dimethylformamide, N-methylpyrrolidone, dimethylacetamide; and alcohols, such as methanol, ethanol, isopropanol, t-BuOH, cyclohenxanol, heptanol, octanol, or longer chain alcohols, and diethyleneglycol; and aromatic hydrocarbons such as toluene and xylenes both as pure isomers and as a mixture of isomers. Preferred organic solvents include tetrahydrofuran, 2-methyl tetrahydrofuran, dioxane, acetonitrile, DMF.

Alternatively it is possible to conduct the reaction in a biphasic system comprising an organic solvent as described above under step ii that are immiscible with water, preferably ethyl acetate, 2-methyl tetrahydrofuran or dichloromethane, and an aqueous solvent, preferably a solution of sodium hydrogen carbonate or sodium carbonate or an organic amine such as triethylamine or diisopropylethylamine. It can also be possible to conduct the reaction in aqueous solvent without addition of base.

The reaction can be carried out at a temperature from 0° C. to 100° C., preferably from 20° C. to 70° C., in particular at 50° C. (e.g. no lower than 0° C., preferably no lower than 20° C., e.g. no more than 100° C., preferably no more than 70° C.). A temperature no lower than 20° C. is preferred to reduce reaction times.

Compounds of formula (I) can be isolated in a free form or as salts formed by adding an acid to compounds of formula (I) in a free base form. Suitable acids include mineral acids and organic acids such as HCl, HBr, $H_2SO_4$, acetic acid, methanesulfonic acids, p-methylphenylsulfonic acids, oxalic acid and trifluoroacetic acid.

Steps 1-1, 1-2 and 1-3

This is described under Scheme 3 below. Steps i, ii and 1-1, 1-2 and 1-3 can be conducted in the same reaction vessel (one-pot reaction) without isolation of the compound of formula (I). In other words, compound of formula (VIII), (IX) and (X) can be prepared from the compound of formula (V) without isolation of the compound of formula (VI) or (I).

Scheme 3

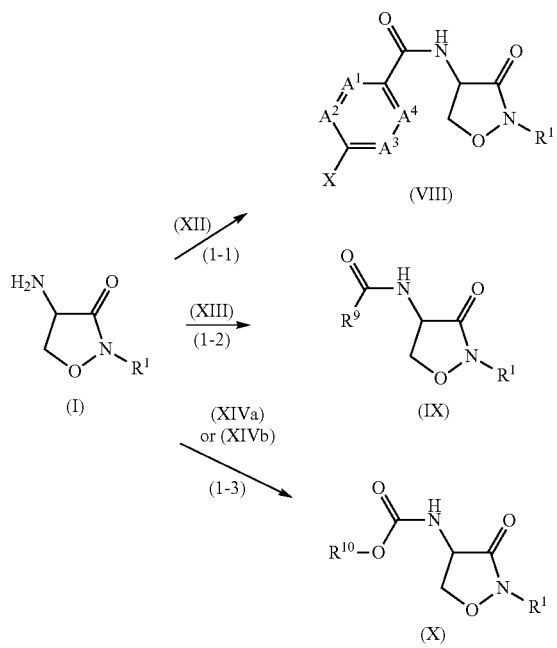

Step 1-1

Compounds of formula (VIII) can be prepared by reacting a compound of formula (I) with a compound of formula (XII) wherein the substituents are defined as herein disclosed. When $R^8$ is hydroxy such reactions are usually carried out in the presence of a coupling reagent, such as N,N'-dicyclohexylcarbodiimide ("DCC"), 1-ethyl-3-(3-dimethylamino-propyl)carbodiimide hydrochloride ("EDC") or bis(2-oxo-3-oxazolidinyl)phosphonic chloride ("BOP-Cl"), in the presence of a base, and optionally in the presence of a nucleophilic catalyst, such as hydroxybenzotriazole ("HOBT").

Suitable bases include carbonates, hydroxides, nitrogen-based organic bases such as amines, pyridines and derivatives thereof, e.g. $Na_2CO_3$, $K_2CO_3$, $NaHCO_3$, NaOH, triethylamine, pyridine, N-methyl morpholine and diisopropylethylamine.

Suitable solvents include, but are not limited to polar organic solvents, e.g. halogenated organic solvents or ethers such as chloroform, dichloromethane, dichloroethane, monochlorobenzene, dichlorobenzene, trichlorobenzene, 4-fluorotoluene, THF, 2-methyl THF, dioxane, dimethoxyethane, toluene, acetonitrile and xylenes preferably chloroform, dichloromethane or THF.

When $R^8$ is chloro such reactions are usually carried out in the presence of a base, and optionally in the presence of a nucleophilic catalyst such as 4-dimethylamino pyridine ("DMAP").

Suitable bases include carbonates, hydroxides, nitrogen-based organic bases such as amines, pyridines and derivatives thereof, e.g. $Na_2CO_3$, $K_2CO_3$, $NaHCO_3$, NaOH, triethylamine, pyridine, N-methyl morpholine and diisopropylethylamine.

Examples of solvents include ethers, such as diethylether, 1,2-dimethoxyethane, diethoxymethane, diglyme, t-butyl methyl ether, THF, 2-methyl-THF, dioxane; halogenated solvents such as chloroform, dichloromethane, dichloroethane, monochlorobenzene, dichlorobenzene, trichlorobenzene, 4-fluorotoluene; esters and ketones such as ethyl acetate, acetone 2-butanone, methylisobutylketone; anisole, polar aprotic solvents such as acetonitrile, dimethylsulfoxide, dimethylformamide, N-methylpyrrolidone and dimethylacetamide, aromatic hydrocarbons such as toluene and xylenes both as pure isomers and as a mixture of isomers. Preferred solvents are dichloromethane, dichloroethane, ethyl acetate, THF, 2-methyl tetrahydrofuran or dioxane.

Alternatively, it is possible to conduct the reaction in a biphasic system comprising an organic solvent, preferably ethyl acetate, toluene, xylenes as single isomers or as a mixture of isomers or dichloromethane, and an aqueous solvent, preferably a solution of sodium hydrogen carbonate or sodium carbonate or an organic amine such as triethylamine or diisopropylethyl amine.

The reaction can be carried out at a temperature from 0° C. to 100° C., preferably from 15° C. to 30° C., in particular at ambient temperature (e.g. no lower than 0° C., preferably no lower than 15° C., e.g. no more than 100° C., preferably no more than 30° C.).

Step 1-2

Compounds of formula (IX), wherein $R^9$ is as defined above, can be prepared under the conditions as described under 1-1 by reacting a compound of formula (I) with a compound of formula (XIII) wherein the substituents are defined as herein disclosed.

Step 1-3

Compounds of formula X can be prepared by reacting compounds of formula (I) with a compound according to formula (XIVa) or (XIVb). An example of a compound according to formula (XIVa) di-tert-butyl dicarbonate in a presence of base. Suitable bases include carbonates, hydroxides, nitrogen-based organic bases such as amines, pyridines and derivatives thereof, e.g. $Na_2CO_3$, $K_2CO_3$, $NaHCO_3$, NaOH, triethylamine, pyridine, N-methyl morpholine and diisopropylethylamine.

Examples of solvents include ethers, such as diethylether, 1,2-dimethoxyethane, diethoxymethane, diglyme, t-butyl methyl ether, THF, 2-methyl-THF, dioxane; halogenated solvents such as chloroform, dichloromethane, dichloroethane, monochlorobenzene, dichlorobenzene, trichlorobenzene, 4-fluorotoluene; esters and ketones such as ethyl acetate, acetone 2-butanone, methylisobutylketone; anisole, polar aprotic solvents such as acetonitrile, dimethylsulfoxide, dimethylformamide, N-methylpyrrolidone, dimethylacetamide; and alcohols, such as methanol, ethanol, isopropanol, t-BuOH, cyclohenxanol, heptanol, octanol, or longer chain alcohols, and diethyleneglycol; aromatic hydrocarbons such as toluene and xylenes both as pure isomers and as a mixture of isomers. Preferred solvents are dichloromethane, dichloroethane, ethyl acetate, THF, or dioxane. Alternatively it is possible to conduct the reaction in the mixture of these solvents and water.

Alternatively it is possible to conduct the reaction in a biphasic system comprising an organic solvent as described above under 1-3, preferably ethyl acetate, toluene, xylene or dichloromethane, and an aqueous base, preferably a solution of sodium hydrogen carbonate or sodium carbonate.

The reaction can be carried out at a temperature from −20° C. to 100° C., preferably from 0° C. to 40° C., in particular at ambient temperature (e.g. no lower than −20° C., preferably no lower than 0° C., e.g. no more than 100° C., preferably no more than 40° C.).

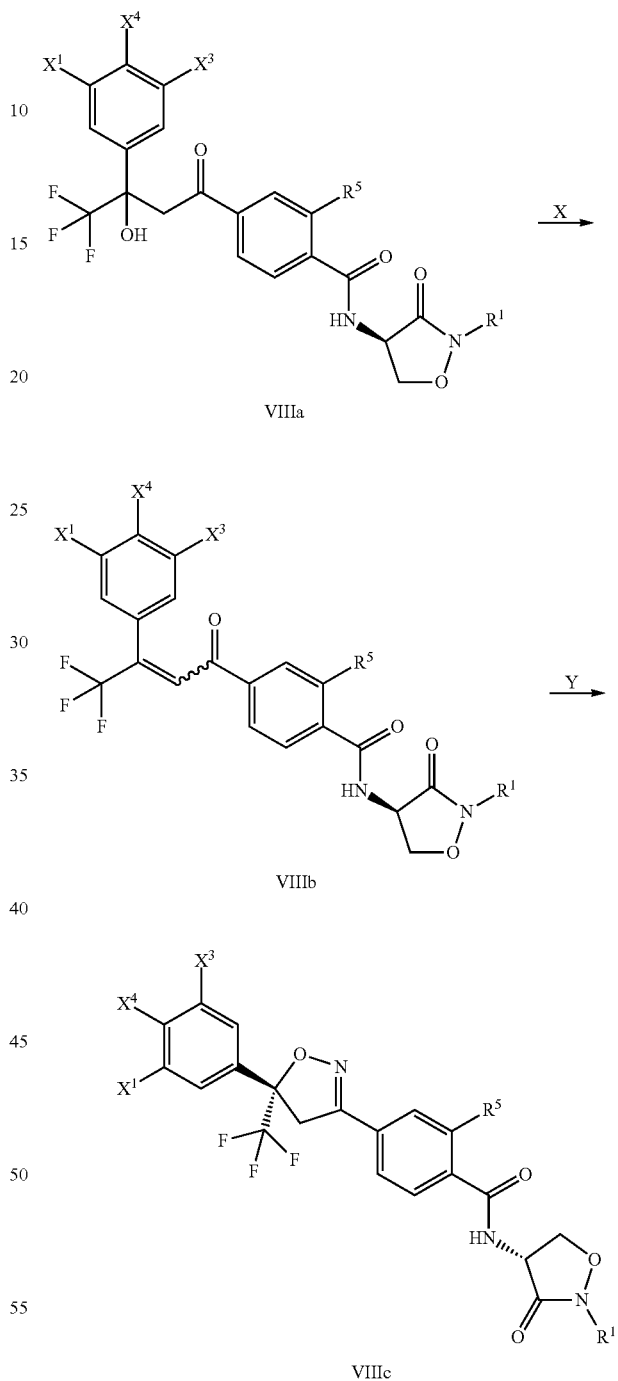

Scheme 4 illustrates how compounds of formula (VIII) may be reacted to produce insecticidally active compounds as described in WO2011/067272 and WO2013/069731, with reaction conditions described therein. Other methods of arriving at compounds of formula (VIIIc) using the present invention will be apparent to the person skilled in the art, and are also described in WO2011/067272. Possible combinations of substituents are shown in Table 1.

TABLE 1

| | X1 | X4 | X3 | R5 | R1 | | X1 | X4 | X3 | R5 | R1 |
|---|---|---|---|---|---|---|---|---|---|---|---|
| 1 | Br | H | H | CH3 | CH2CF3 | 397 | Br | H | H | CH3 | CH2CH3 |
| 2 | Cl | H | H | CH3 | CH2CF3 | 398 | Cl | H | H | CH3 | CH2CH3 |
| 3 | F | H | H | CH3 | CH2CF3 | 399 | F | H | H | CH3 | CH2CH3 |
| 4 | CF3 | H | H | CH3 | CH2CF3 | 400 | CF3 | H | H | CH3 | CH2CH3 |
| 5 | H | Br | H | CH3 | CH2CF3 | 401 | H | Br | H | CH3 | CH2CH3 |
| 6 | Br | Br | H | CH3 | CH2CF3 | 402 | Br | Br | H | CH3 | CH2CH3 |
| 7 | Cl | Br | H | CH3 | CH2CF3 | 403 | Cl | Br | H | CH3 | CH2CH3 |
| 8 | F | Br | H | CH3 | CH2CF3 | 404 | F | Br | H | CH3 | CH2CH3 |
| 9 | CF3 | Br | H | CH3 | CH2CF3 | 405 | CF3 | Br | H | CH3 | CH2CH3 |
| 10 | H | Cl | H | CH3 | CH2CF3 | 406 | H | Cl | H | CH3 | CH2CH3 |
| 11 | Br | Cl | H | CH3 | CH2CF3 | 407 | Br | Cl | H | CH3 | CH2CH3 |
| 12 | Cl | Cl | H | CH3 | CH2CF3 | 408 | Cl | Cl | H | CH3 | CH2CH3 |
| 13 | F | Cl | H | CH3 | CH2CF3 | 409 | F | Cl | H | CH3 | CH2CH3 |
| 14 | CF3 | Cl | H | CH3 | CH2CF3 | 410 | CF3 | Cl | H | CH3 | CH2CH3 |
| 15 | H | F | H | CH3 | CH2CF3 | 411 | H | F | H | CH3 | CH2CH3 |
| 16 | Br | F | H | CH3 | CH2CF3 | 412 | Br | F | H | CH3 | CH2CH3 |
| 17 | Cl | F | H | CH3 | CH2CF3 | 413 | Cl | F | H | CH3 | CH2CH3 |
| 18 | F | F | H | CH3 | CH2CF3 | 414 | F | F | H | CH3 | CH2CH3 |
| 19 | CF3 | F | H | CH3 | CH2CF3 | 415 | CF3 | F | H | CH3 | CH2CH3 |
| 20 | H | H | Br | CH3 | CH2CF3 | 416 | H | H | Br | CH3 | CH2CH3 |
| 21 | Br | H | Br | CH3 | CH2CF3 | 417 | Br | H | Br | CH3 | CH2CH3 |
| 22 | Cl | H | Br | CH3 | CH2CF3 | 418 | Cl | H | Br | CH3 | CH2CH3 |
| 23 | F | H | Br | CH3 | CH2CF3 | 419 | F | H | Br | CH3 | CH2CH3 |
| 24 | CF3 | H | Br | CH3 | CH2CF3 | 420 | CF3 | H | Br | CH3 | CH2CH3 |
| 25 | H | Br | Br | CH3 | CH2CF3 | 421 | H | Br | Br | CH3 | CH2CH3 |
| 26 | Br | Br | Br | CH3 | CH2CF3 | 422 | Br | Br | Br | CH3 | CH2CH3 |
| 27 | Cl | Br | Br | CH3 | CH2CF3 | 423 | Cl | Br | Br | CH3 | CH2CH3 |
| 28 | F | Br | Br | CH3 | CH2CF3 | 424 | F | Br | Br | CH3 | CH2CH3 |
| 29 | CF3 | Br | Br | CH3 | CH2CF3 | 425 | CF3 | Br | Br | CH3 | CH2CH3 |
| 30 | H | Cl | Br | CH3 | CH2CF3 | 426 | H | Cl | Br | CH3 | CH2CH3 |
| 31 | Br | Cl | Br | CH3 | CH2CF3 | 427 | Br | Cl | Br | CH3 | CH2CH3 |
| 32 | Cl | Cl | Br | CH3 | CH2CF3 | 428 | Cl | Cl | Br | CH3 | CH2CH3 |
| 33 | F | Cl | Br | CH3 | CH2CF3 | 429 | F | Cl | Br | CH3 | CH2CH3 |
| 34 | CF3 | Cl | Br | CH3 | CH2CF3 | 430 | CF3 | Cl | Br | CH3 | CH2CH3 |
| 35 | H | F | Br | CH3 | CH2CF3 | 431 | H | F | Br | CH3 | CH2CH3 |
| 36 | Br | F | Br | CH3 | CH2CF3 | 432 | Br | F | Br | CH3 | CH2CH3 |
| 37 | Cl | F | Br | CH3 | CH2CF3 | 433 | Cl | F | Br | CH3 | CH2CH3 |
| 38 | F | F | Br | CH3 | CH2CF3 | 434 | F | F | Br | CH3 | CH2CH3 |
| 39 | CF3 | F | Br | CH3 | CH2CF3 | 435 | CF3 | F | Br | CH3 | CH2CH3 |
| 40 | H | H | Cl | CH3 | CH2CF3 | 436 | H | H | Cl | CH3 | CH2CH3 |
| 41 | Br | H | Cl | CH3 | CH2CF3 | 437 | Br | H | Cl | CH3 | CH2CH3 |
| 42 | Cl | H | Cl | CH3 | CH2CF3 | 438 | Cl | H | Cl | CH3 | CH2CH3 |
| 43 | F | H | Cl | CH3 | CH2CF3 | 439 | F | H | Cl | CH3 | CH2CH3 |
| 44 | CF3 | H | Cl | CH3 | CH2CF3 | 440 | CF3 | H | Cl | CH3 | CH2CH3 |
| 45 | H | Br | Cl | CH3 | CH2CF3 | 441 | H | Br | Cl | CH3 | CH2CH3 |
| 46 | Br | Br | Cl | CH3 | CH2CF3 | 442 | Br | Br | Cl | CH3 | CH2CH3 |
| 47 | Cl | Br | Cl | CH3 | CH2CF3 | 443 | Cl | Br | Cl | CH3 | CH2CH3 |
| 48 | F | Br | Cl | CH3 | CH2CF3 | 444 | F | Br | Cl | CH3 | CH2CH3 |
| 49 | CF3 | Br | Cl | CH3 | CH2CF3 | 445 | CF3 | Br | Cl | CH3 | CH2CH3 |
| 50 | H | Cl | Cl | CH3 | CH2CF3 | 446 | H | Cl | Cl | CH3 | CH2CH3 |
| 51 | Br | Cl | Cl | CH3 | CH2CF3 | 447 | Br | Cl | Cl | CH3 | CH2CH3 |
| 52 | Cl | Cl | Cl | CH3 | CH2CF3 | 448 | Cl | Cl | Cl | CH3 | CH2CH3 |
| 53 | F | Cl | Cl | CH3 | CH2CF3 | 449 | F | Cl | Cl | CH3 | CH2CH3 |
| 54 | CF3 | Cl | Cl | CH3 | CH2CF3 | 450 | CF3 | Cl | Cl | CH3 | CH2CH3 |
| 55 | H | F | Cl | CH3 | CH2CF3 | 451 | H | F | Cl | CH3 | CH2CH3 |
| 56 | Br | F | Cl | CH3 | CH2CF3 | 452 | Br | F | Cl | CH3 | CH2CH3 |
| 57 | Cl | F | Cl | CH3 | CH2CF3 | 453 | Cl | F | Cl | CH3 | CH2CH3 |
| 58 | F | F | Cl | CH3 | CH2CF3 | 454 | F | F | Cl | CH3 | CH2CH3 |
| 59 | CF3 | F | Cl | CH3 | CH2CF3 | 455 | CF3 | F | Cl | CH3 | CH2CH3 |
| 60 | H | H | F | CH3 | CH2CF3 | 456 | H | H | F | CH3 | CH2CH3 |
| 61 | Br | H | F | CH3 | CH2CF3 | 457 | Br | H | F | CH3 | CH2CH3 |
| 62 | Cl | H | F | CH3 | CH2CF3 | 458 | Cl | H | F | CH3 | CH2CH3 |
| 63 | F | H | F | CH3 | CH2CF3 | 459 | F | H | F | CH3 | CH2CH3 |
| 64 | CF3 | H | F | CH3 | CH2CF3 | 460 | CF3 | H | F | CH3 | CH2CH3 |
| 65 | H | Br | F | CH3 | CH2CF3 | 461 | H | Br | F | CH3 | CH2CH3 |
| 66 | Br | Br | F | CH3 | CH2CF3 | 462 | Br | Br | F | CH3 | CH2CH3 |
| 67 | Cl | Br | F | CH3 | CH2CF3 | 463 | Cl | Br | F | CH3 | CH2CH3 |
| 68 | F | Br | F | CH3 | CH2CF3 | 464 | F | Br | F | CH3 | CH2CH3 |
| 69 | CF3 | Br | F | CH3 | CH2CF3 | 465 | CF3 | Br | F | CH3 | CH2CH3 |
| 70 | H | Cl | F | CH3 | CH2CF3 | 466 | H | Cl | F | CH3 | CH2CH3 |
| 71 | Br | Cl | F | CH3 | CH2CF3 | 467 | Br | Cl | F | CH3 | CH2CH3 |
| 72 | Cl | Cl | F | CH3 | CH2CF3 | 468 | Cl | Cl | F | CH3 | CH2CH3 |
| 73 | F | Cl | F | CH3 | CH2CF3 | 469 | F | Cl | F | CH3 | CH2CH3 |
| 74 | CF3 | Cl | F | CH3 | CH2CF3 | 470 | CF3 | Cl | F | CH3 | CH2CH3 |
| 75 | H | F | F | CH3 | CH2CF3 | 471 | H | F | F | CH3 | CH2CH3 |
| 76 | Br | F | F | CH3 | CH2CF3 | 472 | Br | F | F | CH3 | CH2CH3 |
| 77 | Cl | F | F | CH3 | CH2CF3 | 473 | Cl | F | F | CH3 | CH2CH3 |
| 78 | F | F | F | CH3 | CH2CF3 | 474 | F | F | F | CH3 | CH2CH3 |

TABLE 1-continued

| | X1 | X4 | X3 | R5 | R1 | | X1 | X4 | X3 | R5 | R1 |
|---|---|---|---|---|---|---|---|---|---|---|---|
| 79 | CF3 | F | F | CH3 | CH2CF3 | 475 | CF3 | F | F | CH3 | CH2CH3 |
| 80 | H | H | CF3 | CH3 | CH2CF3 | 476 | H | H | CF3 | CH3 | CH2CH3 |
| 81 | Br | H | CF3 | CH3 | CH2CF3 | 477 | Br | H | CF3 | CH3 | CH2CH3 |
| 82 | Cl | H | CF3 | CH3 | CH2CF3 | 478 | Cl | H | CF3 | CH3 | CH2CH3 |
| 83 | F | H | CF3 | CH3 | CH2CF3 | 479 | F | H | CF3 | CH3 | CH2CH3 |
| 84 | CF3 | H | CF3 | CH3 | CH2CF3 | 480 | CF3 | H | CF3 | CH3 | CH2CH3 |
| 85 | H | Br | CF3 | CH3 | CH2CF3 | 481 | H | Br | CF3 | CH3 | CH2CH3 |
| 86 | Br | Br | CF3 | CH3 | CH2CF3 | 482 | Br | Br | CF3 | CH3 | CH2CH3 |
| 87 | Cl | Br | CF3 | CH3 | CH2CF3 | 483 | Cl | Br | CF3 | CH3 | CH2CH3 |
| 88 | F | Br | CF3 | CH3 | CH2CF3 | 484 | F | Br | CF3 | CH3 | CH2CH3 |
| 89 | CF3 | Br | CF3 | CH3 | CH2CF3 | 485 | CF3 | Br | CF3 | CH3 | CH2CH3 |
| 90 | H | Cl | CF3 | CH3 | CH2CF3 | 486 | H | Cl | CF3 | CH3 | CH2CH3 |
| 91 | Br | Cl | CF3 | CH3 | CH2CF3 | 487 | Br | Cl | CF3 | CH3 | CH2CH3 |
| 92 | Cl | Cl | CF3 | CH3 | CH2CF3 | 488 | Cl | Cl | CF3 | CH3 | CH2CH3 |
| 93 | F | Cl | CF3 | CH3 | CH2CF3 | 489 | F | Cl | CF3 | CH3 | CH2CH3 |
| 94 | CF3 | Cl | CF3 | CH3 | CH2CF3 | 490 | CF3 | Cl | CF3 | CH3 | CH2CH3 |
| 95 | H | F | CF3 | CH3 | CH2CF3 | 491 | H | F | CF3 | CH3 | CH2CH3 |
| 96 | Br | F | CF3 | CH3 | CH2CF3 | 492 | Br | F | CF3 | CH3 | CH2CH3 |
| 97 | Cl | F | CF3 | CH3 | CH2CF3 | 493 | Cl | F | CF3 | CH3 | CH2CH3 |
| 98 | F | F | CF3 | CH3 | CH2CF3 | 494 | F | F | CF3 | CH3 | CH2CH3 |
| 99 | CF3 | F | CF3 | CH3 | CH2CF3 | 495 | CF3 | F | CF3 | CH3 | CH2CH3 |
| 100 | Br | H | H | Br | CH2CF3 | 496 | Br | H | H | Br | CH2CH3 |
| 101 | Cl | H | H | Br | CH2CF3 | 497 | Cl | H | H | Br | CH2CH3 |
| 102 | F | H | H | Br | CH2CF3 | 498 | F | H | H | Br | CH2CH3 |
| 103 | CF3 | H | H | Br | CH2CF3 | 499 | CF3 | H | H | Br | CH2CH3 |
| 104 | H | Br | H | Br | CH2CF3 | 500 | H | Br | H | Br | CH2CH3 |
| 105 | Br | Br | H | Br | CH2CF3 | 501 | Br | Br | H | Br | CH2CH3 |
| 106 | Cl | Br | H | Br | CH2CF3 | 502 | Cl | Br | H | Br | CH2CH3 |
| 107 | F | Br | H | Br | CH2CF3 | 503 | F | Br | H | Br | CH2CH3 |
| 108 | CF3 | Br | H | Br | CH2CF3 | 504 | CF3 | Br | H | Br | CH2CH3 |
| 109 | H | Cl | H | Br | CH2CF3 | 505 | H | Cl | H | Br | CH2CH3 |
| 110 | Br | Cl | H | Br | CH2CF3 | 506 | Br | Cl | H | Br | CH2CH3 |
| 111 | Cl | Cl | H | Br | CH2CF3 | 507 | Cl | Cl | H | Br | CH2CH3 |
| 112 | F | Cl | H | Br | CH2CF3 | 508 | F | Cl | H | Br | CH2CH3 |
| 113 | CF3 | Cl | H | Br | CH2CF3 | 509 | CF3 | Cl | H | Br | CH2CH3 |
| 114 | H | F | H | Br | CH2CF3 | 510 | H | F | H | Br | CH2CH3 |
| 115 | Br | F | H | Br | CH2CF3 | 511 | Br | F | H | Br | CH2CH3 |
| 116 | Cl | F | H | Br | CH2CF3 | 512 | Cl | F | H | Br | CH2CH3 |
| 117 | F | F | H | Br | CH2CF3 | 513 | F | F | H | Br | CH2CH3 |
| 118 | CF3 | F | H | Br | CH2CF3 | 514 | CF3 | F | H | Br | CH2CH3 |
| 119 | H | H | Br | Br | CH2CF3 | 515 | H | H | Br | Br | CH2CH3 |
| 120 | Br | H | Br | Br | CH2CF3 | 516 | Br | H | Br | Br | CH2CH3 |
| 121 | Cl | H | Br | Br | CH2CF3 | 517 | Cl | H | Br | Br | CH2CH3 |
| 122 | F | H | Br | Br | CH2CF3 | 518 | F | H | Br | Br | CH2CH3 |
| 123 | CF3 | H | Br | Br | CH2CF3 | 519 | CF3 | H | Br | Br | CH2CH3 |
| 124 | H | Br | Br | Br | CH2CF3 | 520 | H | Br | Br | Br | CH2CH3 |
| 125 | Br | Br | Br | Br | CH2CF3 | 521 | Br | Br | Br | Br | CH2CH3 |
| 126 | Cl | Br | Br | Br | CH2CF3 | 522 | Cl | Br | Br | Br | CH2CH3 |
| 127 | F | Br | Br | Br | CH2CF3 | 523 | F | Br | Br | Br | CH2CH3 |
| 128 | CF3 | Br | Br | Br | CH2CF3 | 524 | CF3 | Br | Br | Br | CH2CH3 |
| 129 | H | Cl | Br | Br | CH2CF3 | 525 | H | Cl | Br | Br | CH2CH3 |
| 130 | Br | Cl | Br | Br | CH2CF3 | 526 | Br | Cl | Br | Br | CH2CH3 |
| 131 | Cl | Cl | Br | Br | CH2CF3 | 527 | Cl | Cl | Br | Br | CH2CH3 |
| 132 | F | Cl | Br | Br | CH2CF3 | 528 | F | Cl | Br | Br | CH2CH3 |
| 133 | CF3 | Cl | Br | Br | CH2CF3 | 529 | CF3 | Cl | Br | Br | CH2CH3 |
| 134 | H | F | Br | Br | CH2CF3 | 530 | H | F | Br | Br | CH2CH3 |
| 135 | Br | F | Br | Br | CH2CF3 | 531 | Br | F | Br | Br | CH2CH3 |
| 136 | Cl | F | Br | Br | CH2CF3 | 532 | Cl | F | Br | Br | CH2CH3 |
| 137 | F | F | Br | Br | CH2CF3 | 533 | F | F | Br | Br | CH2CH3 |
| 138 | CF3 | F | Br | Br | CH2CF3 | 534 | CF3 | F | Br | Br | CH2CH3 |
| 139 | H | H | Cl | Br | CH2CF3 | 535 | H | H | Cl | Br | CH2CH3 |
| 140 | Br | H | Cl | Br | CH2CF3 | 536 | Br | H | Cl | Br | CH2CH3 |
| 141 | Cl | H | Cl | Br | CH2CF3 | 537 | Cl | H | Cl | Br | CH2CH3 |
| 142 | F | H | Cl | Br | CH2CF3 | 538 | F | H | Cl | Br | CH2CH3 |
| 143 | CF3 | H | Cl | Br | CH2CF3 | 539 | CF3 | H | Cl | Br | CH2CH3 |
| 144 | H | Br | Cl | Br | CH2CF3 | 540 | H | Br | Cl | Br | CH2CH3 |
| 145 | Br | Br | Cl | Br | CH2CF3 | 541 | Br | Br | Cl | Br | CH2CH3 |
| 146 | Cl | Br | Cl | Br | CH2CF3 | 542 | Cl | Br | Cl | Br | CH2CH3 |
| 147 | F | Br | Cl | Br | CH2CF3 | 543 | F | Br | Cl | Br | CH2CH3 |
| 148 | CF3 | Br | Cl | Br | CH2CF3 | 544 | CF3 | Br | Cl | Br | CH2CH3 |
| 149 | H | Cl | Cl | Br | CH2CF3 | 545 | H | Cl | Cl | Br | CH2CH3 |
| 150 | Br | Cl | Cl | Br | CH2CF3 | 546 | Br | Cl | Cl | Br | CH2CH3 |
| 151 | Cl | Cl | Cl | Br | CH2CF3 | 547 | Cl | Cl | Cl | Br | CH2CH3 |
| 152 | F | Cl | Cl | Br | CH2CF3 | 548 | F | Cl | Cl | Br | CH2CH3 |
| 153 | CF3 | Cl | Cl | Br | CH2CF3 | 549 | CF3 | Cl | Cl | Br | CH2CH3 |
| 154 | H | F | Cl | Br | CH2CF3 | 550 | H | F | Cl | Br | CH2CH3 |
| 155 | Br | F | Cl | Br | CH2CF3 | 551 | Br | F | Cl | Br | CH2CH3 |
| 156 | Cl | F | Cl | Br | CH2CF3 | 552 | Cl | F | Cl | Br | CH2CH3 |

TABLE 1-continued

| | X1 | X4 | X3 | R5 | R1 | | X1 | X4 | X3 | R5 | R1 |
|---|---|---|---|---|---|---|---|---|---|---|---|
| 157 | F | F | Cl | Br | CH2CF3 | 553 | F | F | Cl | Br | CH2CH3 |
| 158 | CF3 | F | Cl | Br | CH2CF3 | 554 | CF3 | F | Cl | Br | CH2CH3 |
| 159 | H | H | F | Br | CH2CF3 | 555 | H | H | F | Br | CH2CH3 |
| 160 | Br | H | F | Br | CH2CF3 | 556 | Br | H | F | Br | CH2CH3 |
| 161 | Cl | H | F | Br | CH2CF3 | 557 | Cl | H | F | Br | CH2CH3 |
| 162 | F | H | F | Br | CH2CF3 | 558 | F | H | F | Br | CH2CH3 |
| 163 | CF3 | H | F | Br | CH2CF3 | 559 | CF3 | H | F | Br | CH2CH3 |
| 164 | H | Br | F | Br | CH2CF3 | 560 | H | Br | F | Br | CH2CH3 |
| 165 | Br | Br | F | Br | CH2CF3 | 561 | Br | Br | F | Br | CH2CH3 |
| 166 | Cl | Br | F | Br | CH2CF3 | 562 | Cl | Br | F | Br | CH2CH3 |
| 167 | F | Br | F | Br | CH2CF3 | 563 | F | Br | F | Br | CH2CH3 |
| 168 | CF3 | Br | F | Br | CH2CF3 | 564 | CF3 | Br | F | Br | CH2CH3 |
| 169 | H | Cl | F | Br | CH2CF3 | 565 | H | Cl | F | Br | CH2CH3 |
| 170 | Br | Cl | F | Br | CH2CF3 | 566 | Br | Cl | F | Br | CH2CH3 |
| 171 | Cl | Cl | F | Br | CH2CF3 | 567 | Cl | Cl | F | Br | CH2CH3 |
| 172 | F | Cl | F | Br | CH2CF3 | 568 | F | Cl | F | Br | CH2CH3 |
| 173 | CF3 | Cl | F | Br | CH2CF3 | 569 | CF3 | Cl | F | Br | CH2CH3 |
| 174 | H | F | F | Br | CH2CF3 | 570 | H | F | F | Br | CH2CH3 |
| 175 | Br | F | F | Br | CH2CF3 | 571 | Br | F | F | Br | CH2CH3 |
| 176 | Cl | F | F | Br | CH2CF3 | 572 | Cl | F | F | Br | CH2CH3 |
| 177 | F | F | F | Br | CH2CF3 | 573 | F | F | F | Br | CH2CH3 |
| 178 | CF3 | F | F | Br | CH2CF3 | 574 | CF3 | F | F | Br | CH2CH3 |
| 179 | H | H | CF3 | Br | CH2CF3 | 575 | H | H | CF3 | Br | CH2CH3 |
| 180 | Br | H | CF3 | Br | CH2CF3 | 576 | Br | H | CF3 | Br | CH2CH3 |
| 181 | Cl | H | CF3 | Br | CH2CF3 | 577 | Cl | H | CF3 | Br | CH2CH3 |
| 182 | F | H | CF3 | Br | CH2CF3 | 578 | F | H | CF3 | Br | CH2CH3 |
| 183 | CF3 | H | CF3 | Br | CH2CF3 | 579 | CF3 | H | CF3 | Br | CH2CH3 |
| 184 | H | Br | CF3 | Br | CH2CF3 | 580 | H | Br | CF3 | Br | CH2CH3 |
| 185 | Br | Br | CF3 | Br | CH2CF3 | 581 | Br | Br | CF3 | Br | CH2CH3 |
| 186 | Cl | Br | CF3 | Br | CH2CF3 | 582 | Cl | Br | CF3 | Br | CH2CH3 |
| 187 | F | Br | CF3 | Br | CH2CF3 | 583 | F | Br | CF3 | Br | CH2CH3 |
| 188 | CF3 | Br | CF3 | Br | CH2CF3 | 584 | CF3 | Br | CF3 | Br | CH2CH3 |
| 189 | H | Cl | CF3 | Br | CH2CF3 | 585 | H | Cl | CF3 | Br | CH2CH3 |
| 190 | Br | Cl | CF3 | Br | CH2CF3 | 586 | Br | Cl | CF3 | Br | CH2CH3 |
| 191 | Cl | Cl | CF3 | Br | CH2CF3 | 587 | Cl | Cl | CF3 | Br | CH2CH3 |
| 192 | F | Cl | CF3 | Br | CH2CF3 | 588 | F | Cl | CF3 | Br | CH2CH3 |
| 193 | CF3 | Cl | CF3 | Br | CH2CF3 | 589 | CF3 | Cl | CF3 | Br | CH2CH3 |
| 194 | H | F | CF3 | Br | CH2CF3 | 590 | H | F | CF3 | Br | CH2CH3 |
| 195 | Br | F | CF3 | Br | CH2CF3 | 591 | Br | F | CF3 | Br | CH2CH3 |
| 196 | Cl | F | CF3 | Br | CH2CF3 | 592 | Cl | F | CF3 | Br | CH2CH3 |
| 197 | F | F | CF3 | Br | CH2CF3 | 593 | F | F | CF3 | Br | CH2CH3 |
| 198 | CF3 | F | CF3 | Br | CH2CF3 | 594 | CF3 | F | CF3 | Br | CH2CH3 |
| 199 | Br | H | H | Cl | CH2CF3 | 595 | Br | H | H | Cl | CH2CH3 |
| 200 | Cl | H | H | Cl | CH2CF3 | 596 | Cl | H | H | Cl | CH2CH3 |
| 201 | F | H | H | Cl | CH2CF3 | 597 | F | H | H | Cl | CH2CH3 |
| 202 | CF3 | H | H | Cl | CH2CF3 | 598 | CF3 | H | H | Cl | CH2CH3 |
| 203 | H | Br | H | Cl | CH2CF3 | 599 | H | Br | H | Cl | CH2CH3 |
| 204 | Br | Br | H | Cl | CH2CF3 | 600 | Br | Br | H | Cl | CH2CH3 |
| 205 | Cl | Br | H | Cl | CH2CF3 | 601 | Cl | Br | H | Cl | CH2CH3 |
| 206 | F | Br | H | Cl | CH2CF3 | 602 | F | Br | H | Cl | CH2CH3 |
| 207 | CF3 | Br | H | Cl | CH2CF3 | 603 | CF3 | Br | H | Cl | CH2CH3 |
| 208 | H | Cl | H | Cl | CH2CF3 | 604 | H | Cl | H | Cl | CH2CH3 |
| 209 | Br | Cl | H | Cl | CH2CF3 | 605 | Br | Cl | H | Cl | CH2CH3 |
| 210 | Cl | Cl | H | Cl | CH2CF3 | 606 | Cl | Cl | H | Cl | CH2CH3 |
| 211 | F | Cl | H | Cl | CH2CF3 | 607 | F | Cl | H | Cl | CH2CH3 |
| 212 | CF3 | Cl | H | Cl | CH2CF3 | 608 | CF3 | Cl | H | Cl | CH2CH3 |
| 213 | H | F | H | Cl | CH2CF3 | 609 | H | F | H | Cl | CH2CH3 |
| 214 | Br | F | H | Cl | CH2CF3 | 610 | Br | F | H | Cl | CH2CH3 |
| 215 | Cl | F | H | Cl | CH2CF3 | 611 | Cl | F | H | Cl | CH2CH3 |
| 216 | F | F | H | Cl | CH2CF3 | 612 | F | F | H | Cl | CH2CH3 |
| 217 | CF3 | F | H | Cl | CH2CF3 | 613 | CF3 | F | H | Cl | CH2CH3 |
| 218 | H | H | Br | Cl | CH2CF3 | 614 | H | H | Br | Cl | CH2CH3 |
| 219 | Br | H | Br | Cl | CH2CF3 | 615 | Br | H | Br | Cl | CH2CH3 |
| 220 | Cl | H | Br | Cl | CH2CF3 | 616 | Cl | H | Br | Cl | CH2CH3 |
| 221 | F | H | Br | Cl | CH2CF3 | 617 | F | H | Br | Cl | CH2CH3 |
| 222 | CF3 | H | Br | Cl | CH2CF3 | 618 | CF3 | H | Br | Cl | CH2CH3 |
| 223 | H | Br | Br | Cl | CH2CF3 | 619 | H | Br | Br | Cl | CH2CH3 |
| 224 | Br | Br | Br | Cl | CH2CF3 | 620 | Br | Br | Br | Cl | CH2CH3 |
| 225 | Cl | Br | Br | Cl | CH2CF3 | 621 | Cl | Br | Br | Cl | CH2CH3 |
| 226 | F | Br | Br | Cl | CH2CF3 | 622 | F | Br | Br | Cl | CH2CH3 |
| 227 | CF3 | Br | Br | Cl | CH2CF3 | 623 | CF3 | Br | Br | Cl | CH2CH3 |
| 228 | H | Cl | Br | Cl | CH2CF3 | 624 | H | Cl | Br | Cl | CH2CH3 |
| 229 | Br | Cl | Br | Cl | CH2CF3 | 625 | Br | Cl | Br | Cl | CH2CH3 |
| 230 | Cl | Cl | Br | Cl | CH2CF3 | 626 | Cl | Cl | Br | Cl | CH2CH3 |
| 231 | F | Cl | Br | Cl | CH2CF3 | 627 | F | Cl | Br | Cl | CH2CH3 |
| 232 | CF3 | Cl | Br | Cl | CH2CF3 | 628 | CF3 | Cl | Br | Cl | CH2CH3 |
| 233 | H | F | Br | Cl | CH2CF3 | 629 | H | F | Br | Cl | CH2CH3 |
| 234 | Br | F | Br | Cl | CH2CF3 | 630 | Br | F | Br | Cl | CH2CH3 |

TABLE 1-continued

| | X1 | X4 | X3 | R5 | R1 | | X1 | X4 | X3 | R5 | R1 |
|---|---|---|---|---|---|---|---|---|---|---|---|
| 235 | Cl | F | Br | Cl | CH2CF3 | 631 | Cl | F | Br | Cl | CH2CH3 |
| 236 | F | F | Br | Cl | CH2CF3 | 632 | F | F | Br | Cl | CH2CH3 |
| 237 | CF3 | F | Br | Cl | CH2CF3 | 633 | CF3 | F | Br | Cl | CH2CH3 |
| 238 | H | H | Cl | Cl | CH2CF3 | 634 | H | H | Cl | Cl | CH2CH3 |
| 239 | Br | H | Cl | Cl | CH2CF3 | 635 | Br | H | Cl | Cl | CH2CH3 |
| 240 | Cl | H | Cl | Cl | CH2CF3 | 636 | Cl | H | Cl | Cl | CH2CH3 |
| 241 | F | H | Cl | Cl | CH2CF3 | 637 | F | H | Cl | Cl | CH2CH3 |
| 242 | CF3 | H | Cl | Cl | CH2CF3 | 638 | CF3 | H | Cl | Cl | CH2CH3 |
| 243 | H | Br | Cl | Cl | CH2CF3 | 639 | H | Br | Cl | Cl | CH2CH3 |
| 244 | Br | Br | Cl | Cl | CH2CF3 | 640 | Br | Br | Cl | Cl | CH2CH3 |
| 245 | Cl | Br | Cl | Cl | CH2CF3 | 641 | Cl | Br | Cl | Cl | CH2CH3 |
| 246 | F | Br | Cl | Cl | CH2CF3 | 642 | F | Br | Cl | Cl | CH2CH3 |
| 247 | CF3 | Br | Cl | Cl | CH2CF3 | 643 | CF3 | Br | Cl | Cl | CH2CH3 |
| 248 | H | Cl | Cl | Cl | CH2CF3 | 644 | H | Cl | Cl | Cl | CH2CH3 |
| 249 | Br | Cl | Cl | Cl | CH2CF3 | 645 | Br | Cl | Cl | Cl | CH2CH3 |
| 250 | Cl | Cl | Cl | Cl | CH2CF3 | 646 | Cl | Cl | Cl | Cl | CH2CH3 |
| 251 | F | Cl | Cl | Cl | CH2CF3 | 647 | F | Cl | Cl | Cl | CH2CH3 |
| 252 | CF3 | Cl | Cl | Cl | CH2CF3 | 648 | CF3 | Cl | Cl | Cl | CH2CH3 |
| 253 | H | F | Cl | Cl | CH2CF3 | 649 | H | F | Cl | Cl | CH2CH3 |
| 254 | Br | F | Cl | Cl | CH2CF3 | 650 | Br | F | Cl | Cl | CH2CH3 |
| 255 | Cl | F | Cl | Cl | CH2CF3 | 651 | Cl | F | Cl | Cl | CH2CH3 |
| 256 | F | F | Cl | Cl | CH2CF3 | 652 | F | F | Cl | Cl | CH2CH3 |
| 257 | CF3 | F | Cl | Cl | CH2CF3 | 653 | CF3 | F | Cl | Cl | CH2CH3 |
| 258 | H | H | F | Cl | CH2CF3 | 654 | H | H | F | Cl | CH2CH3 |
| 259 | Br | H | F | Cl | CH2CF3 | 655 | Br | H | F | Cl | CH2CH3 |
| 260 | Cl | H | F | Cl | CH2CF3 | 656 | Cl | H | F | Cl | CH2CH3 |
| 261 | F | H | F | Cl | CH2CF3 | 657 | F | H | F | Cl | CH2CH3 |
| 262 | CF3 | H | F | Cl | CH2CF3 | 658 | CF3 | H | F | Cl | CH2CH3 |
| 263 | H | Br | F | Cl | CH2CF3 | 659 | H | Br | F | Cl | CH2CH3 |
| 264 | Br | Br | F | Cl | CH2CF3 | 660 | Br | Br | F | Cl | CH2CH3 |
| 265 | Cl | Br | F | Cl | CH2CF3 | 661 | Cl | Br | F | Cl | CH2CH3 |
| 266 | F | Br | F | Cl | CH2CF3 | 662 | F | Br | F | Cl | CH2CH3 |
| 267 | CF3 | Br | F | Cl | CH2CF3 | 663 | CF3 | Br | F | Cl | CH2CH3 |
| 268 | H | Cl | F | Cl | CH2CF3 | 664 | H | Cl | F | Cl | CH2CH3 |
| 269 | Br | Cl | F | Cl | CH2CF3 | 665 | Br | Cl | F | Cl | CH2CH3 |
| 270 | Cl | Cl | F | Cl | CH2CF3 | 666 | Cl | Cl | F | Cl | CH2CH3 |
| 271 | F | Cl | F | Cl | CH2CF3 | 667 | F | Cl | F | Cl | CH2CH3 |
| 272 | CF3 | Cl | F | Cl | CH2CF3 | 668 | CF3 | Cl | F | Cl | CH2CH3 |
| 273 | H | F | F | Cl | CH2CF3 | 669 | H | F | F | Cl | CH2CH3 |
| 274 | Br | F | F | Cl | CH2CF3 | 670 | Br | F | F | Cl | CH2CH3 |
| 275 | Cl | F | F | Cl | CH2CF3 | 671 | Cl | F | F | Cl | CH2CH3 |
| 276 | F | F | F | Cl | CH2CF3 | 672 | F | F | F | Cl | CH2CH3 |
| 277 | CF3 | F | F | Cl | CH2CF3 | 673 | CF3 | F | F | Cl | CH2CH3 |
| 278 | H | H | CF3 | Cl | CH2CF3 | 674 | H | H | CF3 | Cl | CH2CH3 |
| 279 | Br | H | CF3 | Cl | CH2CF3 | 675 | Br | H | CF3 | Cl | CH2CH3 |
| 280 | Cl | H | CF3 | Cl | CH2CF3 | 676 | Cl | H | CF3 | Cl | CH2CH3 |
| 281 | F | H | CF3 | Cl | CH2CF3 | 677 | F | H | CF3 | Cl | CH2CH3 |
| 282 | CF3 | H | CF3 | Cl | CH2CF3 | 678 | CF3 | H | CF3 | Cl | CH2CH3 |
| 283 | H | Br | CF3 | Cl | CH2CF3 | 679 | H | Br | CF3 | Cl | CH2CH3 |
| 284 | Br | Br | CF3 | Cl | CH2CF3 | 680 | Br | Br | CF3 | Cl | CH2CH3 |
| 285 | Cl | Br | CF3 | Cl | CH2CF3 | 681 | Cl | Br | CF3 | Cl | CH2CH3 |
| 286 | F | Br | CF3 | Cl | CH2CF3 | 682 | F | Br | CF3 | Cl | CH2CH3 |
| 287 | CF3 | Br | CF3 | Cl | CH2CF3 | 683 | CF3 | Br | CF3 | Cl | CH2CH3 |
| 288 | H | Cl | CF3 | Cl | CH2CF3 | 684 | H | Cl | CF3 | Cl | CH2CH3 |
| 289 | Br | Cl | CF3 | Cl | CH2CF3 | 685 | Br | Cl | CF3 | Cl | CH2CH3 |
| 290 | Cl | Cl | CF3 | Cl | CH2CF3 | 686 | Cl | Cl | CF3 | Cl | CH2CH3 |
| 291 | F | Cl | CF3 | Cl | CH2CF3 | 687 | F | Cl | CF3 | Cl | CH2CH3 |
| 292 | CF3 | Cl | CF3 | Cl | CH2CF3 | 688 | CF3 | Cl | CF3 | Cl | CH2CH3 |
| 293 | H | F | CF3 | Cl | CH2CF3 | 689 | H | F | CF3 | Cl | CH2CH3 |
| 294 | Br | F | CF3 | Cl | CH2CF3 | 690 | Br | F | CF3 | Cl | CH2CH3 |
| 295 | Cl | F | CF3 | Cl | CH2CF3 | 691 | Cl | F | CF3 | Cl | CH2CH3 |
| 296 | F | F | CF3 | Cl | CH2CF3 | 692 | F | F | CF3 | Cl | CH2CH3 |
| 297 | CF3 | F | CF3 | Cl | CH2CF3 | 693 | CF3 | F | CF3 | Cl | CH2CH3 |
| 298 | Br | H | H | CF3 | CH2CF3 | 694 | Br | H | H | CF3 | CH2CH3 |
| 299 | Cl | H | H | CF3 | CH2CF3 | 695 | Cl | H | H | CF3 | CH2CH3 |
| 300 | F | H | H | CF3 | CH2CF3 | 696 | F | H | H | CF3 | CH2CH3 |
| 301 | CF3 | H | H | CF3 | CH2CF3 | 697 | CF3 | H | H | CF3 | CH2CH3 |
| 302 | H | Br | H | CF3 | CH2CF3 | 698 | H | Br | H | CF3 | CH2CH3 |
| 303 | Br | Br | H | CF3 | CH2CF3 | 699 | Br | Br | H | CF3 | CH2CH3 |
| 304 | Cl | Br | H | CF3 | CH2CF3 | 700 | Cl | Br | H | CF3 | CH2CH3 |
| 305 | F | Br | H | CF3 | CH2CF3 | 701 | F | Br | H | CF3 | CH2CH3 |
| 306 | CF3 | Br | H | CF3 | CH2CF3 | 702 | CF3 | Br | H | CF3 | CH2CH3 |
| 307 | H | Cl | H | CF3 | CH2CF3 | 703 | H | Cl | H | CF3 | CH2CH3 |
| 308 | Br | Cl | H | CF3 | CH2CF3 | 704 | Br | Cl | H | CF3 | CH2CH3 |
| 309 | Cl | Cl | H | CF3 | CH2CF3 | 705 | Cl | Cl | H | CF3 | CH2CH3 |
| 310 | F | Cl | H | CF3 | CH2CF3 | 706 | F | Cl | H | CF3 | CH2CH3 |
| 311 | CF3 | Cl | H | CF3 | CH2CF3 | 707 | CF3 | Cl | H | CF3 | CH2CH3 |
| 312 | H | F | H | CF3 | CH2CF3 | 708 | H | F | H | CF3 | CH2CH3 |

TABLE 1-continued

| | X1 | X4 | X3 | R5 | R1 | | X1 | X4 | X3 | R5 | R1 |
|---|---|---|---|---|---|---|---|---|---|---|---|
| 313 | Br | F | H | CF3 | CH2CF3 | 709 | Br | F | H | CF3 | CH2CH3 |
| 314 | Cl | F | H | CF3 | CH2CF3 | 710 | Cl | F | H | CF3 | CH2CH3 |
| 315 | F | F | H | CF3 | CH2CF3 | 711 | F | F | H | CF3 | CH2CH3 |
| 316 | CF3 | F | H | CF3 | CH2CF3 | 712 | CF3 | F | H | CF3 | CH2CH3 |
| 317 | H | H | Br | CF3 | CH2CF3 | 713 | H | H | Br | CF3 | CH2CH3 |
| 318 | Br | H | Br | CF3 | CH2CF3 | 714 | Br | H | Br | CF3 | CH2CH3 |
| 319 | Cl | H | Br | CF3 | CH2CF3 | 715 | Cl | H | Br | CF3 | CH2CH3 |
| 320 | F | H | Br | CF3 | CH2CF3 | 716 | F | H | Br | CF3 | CH2CH3 |
| 321 | CF3 | H | Br | CF3 | CH2CF3 | 717 | CF3 | H | Br | CF3 | CH2CH3 |
| 322 | H | Br | Br | CF3 | CH2CF3 | 718 | H | Br | Br | CF3 | CH2CH3 |
| 323 | Br | Br | Br | CF3 | CH2CF3 | 719 | Br | Br | Br | CF3 | CH2CH3 |
| 324 | Cl | Br | Br | CF3 | CH2CF3 | 720 | Cl | Br | Br | CF3 | CH2CH3 |
| 325 | F | Br | Br | CF3 | CH2CF3 | 721 | F | Br | Br | CF3 | CH2CH3 |
| 326 | CF3 | Br | Br | CF3 | CH2CF3 | 722 | CF3 | Br | Br | CF3 | CH2CH3 |
| 327 | H | Cl | Br | CF3 | CH2CF3 | 723 | H | Cl | Br | CF3 | CH2CH3 |
| 328 | Br | Cl | Br | CF3 | CH2CF3 | 724 | Br | Cl | Br | CF3 | CH2CH3 |
| 329 | Cl | Cl | Br | CF3 | CH2CF3 | 725 | Cl | Cl | Br | CF3 | CH2CH3 |
| 330 | F | Cl | Br | CF3 | CH2CF3 | 726 | F | Cl | Br | CF3 | CH2CH3 |
| 331 | CF3 | Cl | Br | CF3 | CH2CF3 | 727 | CF3 | Cl | Br | CF3 | CH2CH3 |
| 332 | H | F | Br | CF3 | CH2CF3 | 728 | H | F | Br | CF3 | CH2CH3 |
| 333 | Br | F | Br | CF3 | CH2CF3 | 729 | Br | F | Br | CF3 | CH2CH3 |
| 334 | Cl | F | Br | CF3 | CH2CF3 | 730 | Cl | F | Br | CF3 | CH2CH3 |
| 335 | F | F | Br | CF3 | CH2CF3 | 731 | F | F | Br | CF3 | CH2CH3 |
| 336 | CF3 | F | Br | CF3 | CH2CF3 | 732 | CF3 | F | Br | CF3 | CH2CH3 |
| 337 | H | H | Cl | CF3 | CH2CF3 | 733 | H | H | Cl | CF3 | CH2CH3 |
| 338 | Br | H | Cl | CF3 | CH2CF3 | 734 | Br | H | Cl | CF3 | CH2CH3 |
| 339 | Cl | H | Cl | CF3 | CH2CF3 | 735 | Cl | H | Cl | CF3 | CH2CH3 |
| 340 | F | H | Cl | CF3 | CH2CF3 | 736 | F | H | Cl | CF3 | CH2CH3 |
| 341 | CF3 | H | Cl | CF3 | CH2CF3 | 737 | CF3 | H | Cl | CF3 | CH2CH3 |
| 342 | H | Br | Cl | CF3 | CH2CF3 | 738 | H | Br | Cl | CF3 | CH2CH3 |
| 343 | Br | Br | Cl | CF3 | CH2CF3 | 739 | Br | Br | Cl | CF3 | CH2CH3 |
| 344 | Cl | Br | Cl | CF3 | CH2CF3 | 740 | Cl | Br | Cl | CF3 | CH2CH3 |
| 345 | F | Br | Cl | CF3 | CH2CF3 | 741 | F | Br | Cl | CF3 | CH2CH3 |
| 346 | CF3 | Br | Cl | CF3 | CH2CF3 | 742 | CF3 | Br | Cl | CF3 | CH2CH3 |
| 347 | H | Cl | Cl | CF3 | CH2CF3 | 743 | H | Cl | Cl | CF3 | CH2CH3 |
| 348 | Br | Cl | Cl | CF3 | CH2CF3 | 744 | Br | Cl | Cl | CF3 | CH2CH3 |
| 349 | Cl | Cl | Cl | CF3 | CH2CF3 | 745 | Cl | Cl | Cl | CF3 | CH2CH3 |
| 350 | F | Cl | Cl | CF3 | CH2CF3 | 746 | F | Cl | Cl | CF3 | CH2CH3 |
| 351 | CF3 | Cl | Cl | CF3 | CH2CF3 | 747 | CF3 | Cl | Cl | CF3 | CH2CH3 |
| 352 | H | F | Cl | CF3 | CH2CF3 | 748 | H | F | Cl | CF3 | CH2CH3 |
| 353 | Br | F | Cl | CF3 | CH2CF3 | 749 | Br | F | Cl | CF3 | CH2CH3 |
| 354 | Cl | F | Cl | CF3 | CH2CF3 | 750 | Cl | F | Cl | CF3 | CH2CH3 |
| 355 | F | F | Cl | CF3 | CH2CF3 | 751 | F | F | Cl | CF3 | CH2CH3 |
| 356 | CF3 | F | Cl | CF3 | CH2CF3 | 752 | CF3 | F | Cl | CF3 | CH2CH3 |
| 357 | H | H | F | CF3 | CH2CF3 | 753 | H | H | F | CF3 | CH2CH3 |
| 358 | Br | H | F | CF3 | CH2CF3 | 754 | Br | H | F | CF3 | CH2CH3 |
| 359 | Cl | H | F | CF3 | CH2CF3 | 755 | Cl | H | F | CF3 | CH2CH3 |
| 360 | F | H | F | CF3 | CH2CF3 | 756 | F | H | F | CF3 | CH2CH3 |
| 361 | CF3 | H | F | CF3 | CH2CF3 | 757 | CF3 | H | F | CF3 | CH2CH3 |
| 362 | H | Br | F | CF3 | CH2CF3 | 758 | H | Br | F | CF3 | CH2CH3 |
| 363 | Br | Br | F | CF3 | CH2CF3 | 759 | Br | Br | F | CF3 | CH2CH3 |
| 364 | Cl | Br | F | CF3 | CH2CF3 | 760 | Cl | Br | F | CF3 | CH2CH3 |
| 365 | F | Br | F | CF3 | CH2CF3 | 761 | F | Br | F | CF3 | CH2CH3 |
| 366 | CF3 | Br | F | CF3 | CH2CF3 | 762 | CF3 | Br | F | CF3 | CH2CH3 |
| 367 | H | Cl | F | CF3 | CH2CF3 | 763 | H | Cl | F | CF3 | CH2CH3 |
| 368 | Br | Cl | F | CF3 | CH2CF3 | 764 | Br | Cl | F | CF3 | CH2CH3 |
| 369 | Cl | Cl | F | CF3 | CH2CF3 | 765 | Cl | Cl | F | CF3 | CH2CH3 |
| 370 | F | Cl | F | CF3 | CH2CF3 | 766 | F | Cl | F | CF3 | CH2CH3 |
| 371 | CF3 | Cl | F | CF3 | CH2CF3 | 767 | CF3 | Cl | F | CF3 | CH2CH3 |
| 372 | H | F | F | CF3 | CH2CF3 | 768 | H | F | F | CF3 | CH2CH3 |
| 373 | Br | F | F | CF3 | CH2CF3 | 769 | Br | F | F | CF3 | CH2CH3 |
| 374 | Cl | F | F | CF3 | CH2CF3 | 770 | Cl | F | F | CF3 | CH2CH3 |
| 375 | F | F | F | CF3 | CH2CF3 | 771 | F | F | F | CF3 | CH2CH3 |
| 376 | CF3 | F | F | CF3 | CH2CF3 | 772 | CF3 | F | F | CF3 | CH2CH3 |
| 377 | H | H | CF3 | CF3 | CH2CF3 | 773 | H | H | CF3 | CF3 | CH2CH3 |
| 378 | Br | H | CF3 | CF3 | CH2CF3 | 774 | Br | H | CF3 | CF3 | CH2CH3 |
| 379 | Cl | H | CF3 | CF3 | CH2CF3 | 775 | Cl | H | CF3 | CF3 | CH2CH3 |
| 380 | F | H | CF3 | CF3 | CH2CF3 | 776 | F | H | CF3 | CF3 | CH2CH3 |
| 381 | CF3 | H | CF3 | CF3 | CH2CF3 | 777 | CF3 | H | CF3 | CF3 | CH2CH3 |
| 382 | H | Br | CF3 | CF3 | CH2CF3 | 778 | H | Br | CF3 | CF3 | CH2CH3 |
| 383 | Br | Br | CF3 | CF3 | CH2CF3 | 779 | Br | Br | CF3 | CF3 | CH2CH3 |
| 384 | Cl | Br | CF3 | CF3 | CH2CF3 | 780 | Cl | Br | CF3 | CF3 | CH2CH3 |
| 385 | F | Br | CF3 | CF3 | CH2CF3 | 781 | F | Br | CF3 | CF3 | CH2CH3 |
| 386 | CF3 | Br | CF3 | CF3 | CH2CF3 | 782 | CF3 | Br | CF3 | CF3 | CH2CH3 |
| 387 | H | Cl | CF3 | CF3 | CH2CF3 | 783 | H | Cl | CF3 | CF3 | CH2CH3 |
| 388 | Br | Cl | CF3 | CF3 | CH2CF3 | 784 | Br | Cl | CF3 | CF3 | CH2CH3 |
| 389 | Cl | Cl | CF3 | CF3 | CH2CF3 | 785 | Cl | Cl | CF3 | CF3 | CH2CH3 |
| 390 | F | Cl | CF3 | CF3 | CH2CF3 | 786 | F | Cl | CF3 | CF3 | CH2CH3 |

TABLE 1-continued

| X1 | X4 | X3 | R5 | R1 | X1 | X4 | X3 | R5 | R1 |
|---|---|---|---|---|---|---|---|---|---|
| 391 CF3 | Cl | CF3 | CF3 | CH2CF3 | 787 CF3 | Cl | CF3 | CF3 | CH2CH3 |
| 392 H | F | CF3 | CF3 | CH2CF3 | 788 H | F | CF3 | CF3 | CH2CH3 |
| 393 Br | F | CF3 | CF3 | CH2CF3 | 789 Br | F | CF3 | CF3 | CH2CH3 |
| 394 Cl | F | CF3 | CF3 | CH2CF3 | 790 Cl | F | CF3 | CF3 | CH2CH3 |
| 395 F | F | CF3 | CF3 | CH2CF3 | 791 F | F | CF3 | CF3 | CH2CH3 |
| 396 CF3 | F | CF3 | CF3 | CH2CF3 | 792 CF3 | F | CF3 | CF3 | CH2CH3 |

In an all reactions the pressure is preferably atmospheric pressure unless stated otherwise.

Where a temperature is stated as from X to Y, X and Y are included in the temperature range.

The reactions conditions described above are also applicable when the compounds of formula (I), (III), (IV), (V) and (VI) are compounds of formula (I*), (III*), (IV*), (V*) and (VI*).

The invention will now be described by way of non-limiting Examples.

EXAMPLES

Example 1

Preparation of (R)-4-amino-2-ethylisoxazolidin-3-one

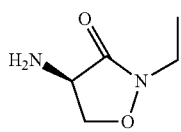

To a solution of N-ethyl(hydroxy)ammonium oxalate (5.5 g, 25.7 mmol) in a mixture of ethanol (70 ml) and water (14 ml), was added dropwise triethylamine (9.8 ml, 70.2 mmol) at ambient temperature and the solution was stirred for 15 min. To this solution (S)-4-(chloromethyl)oxazolidine-2,5-dione (7.0 g, 46.8 mmol) was added in several portions. The resulting reaction mixture was stirred at room temperature for 12 h. The reaction mixture was evaporated under reduced pressure to afford a residue which was purified by trituration with DCM (300 ml) to afford (R)-4-amino-2-ethylisoxazolidin-3-one (3.6 g) as a white solid. $^1$H NMR (400 MHz, CD$_3$OD) δ 4.6 (t, 1H), 4.2-3.9 (m, 2H), 3.7-3.5 (m, 2H), 1.2 (t, 3H).

Example 2 preparation of (R)-4-amino-2-ethylisoxazolidin-3-one

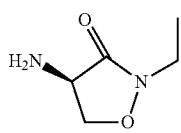

To a solution of N-ethyl(hydroxy)ammonium oxalate (0.42 g, 1.8 mmol) and triethylamine (0.7 ml, 5.0 mmol) in chloroform (3 ml) was added (S)-4-(chloromethyl)oxazolidine-2,5-dione (0.50 g, 3.34 mmol) slowly (in several portions) at room temperature. The resulting reaction mixture was stirred at room temperature for 1 h and then at 50° C. for 1.5 h. The reaction mixture was evaporated under reduced pressure and the desired product was isolated by trituration with DCM to afford (R)-4-amino-2-ethylisoxazolidin-3-one (196 mg) as a white solid. $^1$H NMR (400 MHz, CD$_3$OD) δ 4.6 (t, 1H), 4.2-3.9 (m, 2H), 3.7-3.5 (m, 2H), 1.2 (t, 3H).

Example 3

4-acetyl-N-[(4R)-2-ethyl-3-oxo-isoxazolidin-4-yl)]-2-methyl-benzamide

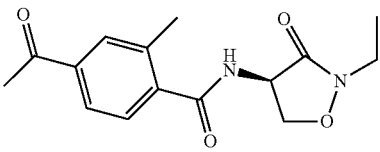 [SMILES: CCN1OC[C@@H](NC(=O)c2ccc(C(C)=O)cc2C)C1=O]

To a suspension of 4-acetyl-2-methyl-benzoic acid (5.0 g, 28 mmol) in dichloromethane (20 ml) was added dimethylformamide (0.2 ml) followed by a dropwise addition of oxalyl chloride (4.6 g, 36.48 mmol). The reaction mixture was stirred at ambient temperature until the end of gas evolution (ca. 4 h). The solvent was evaporated under reduced pressure to afford crude 4-acetyl-2-methyl-benzoyl chloride and it was diluted with acetonitrile (20 ml). The above prepared solution was added dropwise to a solution of (R)-4-amino-2-ethylisoxazolidin-3-one (4.6 g, 36 mmol) and potassium carbonate (15.0 g, 110 mmol) in acetonitrile (80 ml) at 0° C. The reaction mixture was allowed to warm to room temperature and stirred for further 2 h before being evaporated under reduced pressure. Additional water was added and the aqueous phase was extracted with DCM (3×50 ml). The organic phase was evaporated under reduced pressure. The crude product was purified by silica gel chromatography (0-40% ethyl acetate in hexane) to afford 4-acetyl-N-[(4R)-2-ethyl-3-oxo-isoxazolidin-4-yl)]-2-methyl-benzamide (4.3 g) as a pale yellow solid. Chiral HPLC analysis (Chiralpack IA, acetonitrile:THF:water=58:2:40, 0.81 ml/min, retention time 5.29 minutes (major enantiomer 98.3%) and 4.67 minutes (minor enantiomer 1.7%) $^1$H NMR (400 MHz, CDCl$_3$) δ 7.8 (s, 1H), 7.76 (d, 1H), 7.54 (d, 1H), 6.54 (brs, 1H), 4.97 (t, 1H), 4.90-4.80 (m, 1H), 4.10-4.00 (m, 1H), 3.80-3.60 (m, 2H), 2.60 (s, 3H), 2.5 (s, 3H), 1.25 (t, 3H). LC-MS (methanol, ESI): m/z=291 (M+H, RT=1.33).

Example 4 preparation of tert-butyl N-[(4R)-2-ethyl-3-oxo-isoxazolidin-4-yl]carbamate (one pot, step a and 1-3)

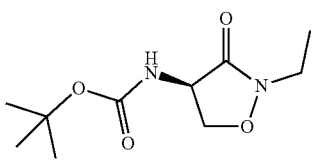 [SMILES: CCN1OC[C@@H](NC(=O)OC(C)(C)C)C1=O]

A solution of N-ethyl(hydroxy)ammonium oxalate (0.16 g, 0.74 mmol) in the mixture of ethanol (2 ml) and water (0.5 ml) was treated with N,N-diisopropylethylamine (0.26 g, 2 mmol) at room temperature for 10 min. (S)-4-(chloromethyl)oxazolidine-2,5-dione (0.2 g, 1.34 mmol) in ethanol (3 ml) was added at 0° C. in one portion. The resulting reaction mixture was stirred at room temperature for 12 h. The reaction mixture was evaporated under reduced pressure to afford crude 4-amino-2-ethylisoxazolidin-3-one as pale yellow gummy mass, diluted with water (5 ml) and THF (10 ml). Triethylamine (0.18 ml, 1.34 mmol) and di-tert-butyl dicarbonate (0.3 g, 1.34 mmol) were added at 0° C. sequentially. The reaction mixture was allowed to warm to room temperature and stirred for further 5 h before being evaporated under reduced pressure. Water (10 ml) was added and the aqueous phase was extracted with DCM (2×25 ml). The combined organic phases were dried over anhydrous $Na_2SO_4$ and evaporated under reduced pressure. The crude product was purified by silica gel chromatography (0-10% EtOAc in cyclohexane) to afforded tert-butyl N-[(4R)-2-ethyl-3-oxo-isoxazolidin-4-yl]carbamate (0.16 g) as a colorless liquid. Chiral HPLC analysis (Chiralpack IA, acetonitrile:THF:water=58:2:40, 0.81 ml/min, retention time 5.43 minutes (major 96.6%) and 4.89 minutes (minor 2.8%).

$^1$H NMR (400 MHz, CDCl$_3$) δ 5.11 (brs, 1H), 4.78-4-67 (m, 1H), 4.59-4.47 (m, 1H), 3.95 (dd, 1H), 3.72-3.54 (m, 2H), 1.45 (s, 9H), 1.23 (t, 3H)

Example 5 preparation of (2S)-2-amino-3-chloro-N-hydroxy-N-(2,2,2-trifluoroethyl)propanamide hydrochloride

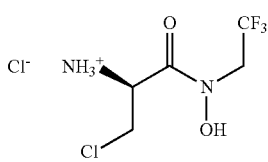 [SMILES: [Cl-] ; [NH3+][C@H](CCl)C(=O)N(O)CC(F)(F)F]

Acetic acid (2 ml) was added to a mixture of (S)-4-(chloromethyl)oxazolidine-2,5-dione (0.50 g, 3.34 mmol) and N-(2,2,2-trifluoroethyl)hydroxylamine hydrochloride (0.56 g, 3.68 mmol). The reaction mixture was stirred at room temperature for 12 h and evaporated under reduced pressure to afford 985 mg of the title compound (75% Quantitative NMR mass purity) as white solid.

$^1$H NMR (400 MHz, CD$_3$OD) δ=4.88-4.85 (m, 1H), 4.51-4.48 (m, 2H), 4.21-4.09 (m, 2H) ppm.

$^{19}$F NMR (400 MHz, DMSO) δ=−71.5 ppm.

Example 6 preparation of (4R)-4-amino-2-(2,2,2-trifluoroethyl)isoxazolidin-3-one

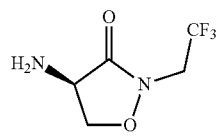 [SMILES: N[C@@H]1CON(CC(F)(F)F)C1=O]

(2S)-2-amino-3-chloro-N-hydroxy-N-(2,2,2-trifluoroethyl)propanamide hydrochloride (0.10 g, 0.27 mmol, 75 mass % purity), potassium carbonate (0.11 g, 0.80 mmol) and acetonitrile (1 ml) was stirred at 0° C. for 1 h and at room temperature for 12 h. The reaction mixture was filtered and evaporated evaporated under reduced pressure giving 25 mg of the title compound (60% Quantitative NMR mass purity) as a white solid.

$^1$H NMR (400 MHz, CD$_3$CN) δ 4.48 (t, 1H), 4.23-4.05 (m, 2H), 3.92-3.81 (m, 2H).

$^{19}$F NMR (400 MHz, DMSO) δ=−69.2 ppm.

Example 7

4-acetyl-2-methyl-N-[(4R)-3-oxo-2-(2,2,2-trifluoroethyl)isoxazolidin-4-yl]benzamide

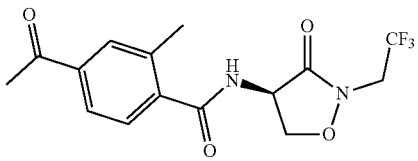 [SMILES: CC(=O)c1ccc(C(=O)N[C@@H]2CON(CC(F)(F)F)C2=O)c(C)c1]

(2S)-2-amino-3-chloro-N-hydroxy-N-(2,2,2-trifluoroethyl)propanamide hydrochloride (150 mg, 0.43 mmol, 75 mass % purity), potassium carbonate (0.28 g, 2.0 mmol) and acetonitrile (2 ml) was stirred at 0° C. for 1 h. A solution of 4-acetyl-2-methyl-benzoyl chloride (138 mg, 0.70 mmol) in acetonitrile (2 ml) was added dropwise at 0° C., and then the reaction mixture was allowed to warm up to room temperature and stirred at this temperature for 1 h. The reaction mixture was filtered and evaporated under reduced pressure. The crude product was purified by silica gel chromatography (0-100% ethyl acetate in hexane) to afford 4-acetyl-2-methyl-N-[(4R)-3-oxo-2-(2,2,2-trifluoroethyl)isoxazolidin-4-yl]benzamide (107 mg) as a white solid. Chiral HPLC analysis (Chiralpack IA, hexane:2-propanol=90:10, 1 ml/min, retention time 13.2 minutes (major 98%) and 15.1 minutes (minor 2%).

$^1$HNMR (CDCl$_3$): δ 7.82 (s, 1H), 7.79 (d, 1H, 8 Hz), 7.52 (d, 1H, 8 Hz), 6.46 (bs, 1H), 5.06-4.93 (m, 1H), 4.31-4.06 (m, 2H), 2.52 (s, 3H) ppm.

$^{19}$F NMR (CDCl$_3$): δ −70.28 ppm

Example 8 preparation of (4R)—N-ethyl-N-hydroxy-2-oxo-oxazolidine-4-carboxamide

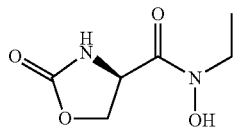

To a suspension of (4R)-2-oxooxazolidine-4-carboxylic acid (0.500 g, 3.81 mmol) in 1,2-dichloroethane (5 ml) was added 3 drops dimethylformamide followed by a dropwise addition of oxalyl chloride (0.543 g, 4.20 mmol). The reaction mixture was stirred at ambient temperature until the end of gas evolution (ca. 1 h). The above prepared solution was added dropwise to a solution of N-ethyl(hydroxy) ammonium oxalate (0.874 g, 4.12 mmol) and triethylamine (1.38 g, 13.5 mmol) in 1,2-dichloroethane (5 ml) at 0° C. The reaction mixture was allowed to warm to room temperature and stirred for further 2 h before being evaporated under reduced pressure. Tetrahydrofuran (20 ml) was added to the residue and the mixture was heated to 40 C for 15 min. The precipitate was filtered off and the filtrate was evaporated under reduced pressure. The crude product was purified by silica gel chromatography (0-5% MeOH in DCM) to afford (4R)—N-ethyl-N-hydroxy-2-oxo-oxazolidine-4-carboxamide (0.409 g) as a light yellow solid. Chiral HPLC analysis (Chiralpack IC, Ethanol:2-propanol=05:95, 1 ml/min, retention time 4.54 minutes (only enantiomer)).

$^1$H NMR (400 MHz, CD$_3$OD) δ 4.84 (m, 1H), 4.67 (t, 1H), 4.33 (dd, 1H), 3.64 (dq, 2H), 1.19 (t, 3H)

Example 9 preparation of (4R)-4-amino-2-ethyl-isoxazolidin-3-one

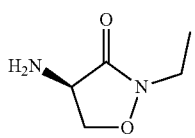

To a solution of (4R)—N-ethyl-N-hydroxy-2-oxo-oxazolidine-4-carboxamide (0.030 g, 0.172 mmol) in THF (0.4 ml) and water (0.13 ml) was added triethylamine (0.035 g, 0.34 mmol) and the resulting reaction mixture was stirred at room temperature for 16 h. Additional water was added and the aqueous phase was extracted with DCM (3×). The aqueous phase was evaporated under reduced pressure to afford (4R)-4-amino-2-ethyl-isoxazolidin-3-one (0.0175 g) as a white solid.

$^1$H NMR (400 MHz, CD$_3$OD) δ 4.6 (t, 1H), 4.2-3.9 (m, 2H), 3.7-3.5 (m, 2H), 1.2 (t, 3H).

Example 10 preparation of tert-butyl N-[(4R)-2-ethyl-3-oxo-isoxazolidin-4-yl]carbamate

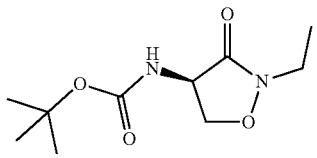 [SMILES: CCN1OC[C@@H](NC(=O)OC(C)(C)C)C1=O]

To a solution of (4R)—N-ethyl-N-hydroxy-2-oxo-oxazolidine-4-carboxamide (0.100 g, 0.574 mmol) in THF (1.2 ml) and water (0.4 ml) was added triethylamine (0.117 g, 1.15 mmol) and the resulting reaction mixture was stirred at room temperature for 16 h. Di-tert-butyl dicarbonate (0.136 g, 0.603 mmol) was added and the reaction mixture was stirred for a further 1 h. Additional water was added and the aqueous phase was extracted with ethyl acetate (3×). The combined organic phases were dried over anhydrous Na$_2$SO$_4$ and evaporated under reduced pressure. The crude product was purified by silica gel chromatography (0-70% EtOAc in cyclohexane) to afford tert-butyl N-[(4R)-2-ethyl-3-oxo-isoxazolidin-4-yl]carbamate (0.0850 g) as a white crystalline solid. Chiral HPLC analysis (Chiralpack IC, heptane:ethanol=80:20, 1 ml/min, retention time 2.85 minutes (minor enantiomer 0.4%) and 4.73 minutes (major enantiomer 99.6%)). $^1$H NMR (400 MHz, CDCl$_3$) δ 5.11 (brs, 1H), 4.78-4-67 (m, 1H), 4.59-4.47 (m, 1H), 3.95 (dd, 1H), 3.72-3.54 (m, 2H), 1.45 (s, 9H), 1.23 (t, 3H)

Alternatively, the Title Compound can be Obtained by Carrying Out the Following Procedure:

To a solution of (4R)—N-ethyl-N-hydroxy-2-oxo-oxazolidine-4-carboxamide (0.100 g, 0.574 mmol) in THF (1.2 ml) and water (0.4 ml) was added K$_2$CO$_3$ (0.0794 g, 0.574 mmol) and the resulting reaction mixture was stirred at room temperature for 16 h. Di-tert-butyl dicarbonate (0.136 g, 0.603 mmol) was added and the reaction mixture was stirred for a further 1 h. Additional water was added and the aqueous phase was extracted with ethyl acetate (3×). The combined organic phases were dried over anhydrous Na$_2$SO$_4$ and evaporated under reduced pressure. The crude product was purified by silica gel chromatography (0-70% EtOAc in cyclohexane) to afford tert-butyl N-[(4R)-2-ethyl-3-oxo-isoxazolidin-4-yl]carbamate (0.070 g) as a white crystalline solid. Chiral HPLC analysis (Chiralpack IC, heptane:ethanol=80:20, 1 ml/min, retention time 2.85 minutes (minor enantiomer 0.4%) and 4.73 minutes (major enantiomer 99.6%)).

Example 11 preparation of (4R)—N-hydroxy-2-oxo-N-phenyl-oxazolidine-4-carboxamide

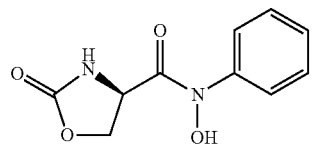 [SMILES: O=C1N[C@@H](C(=O)N(O)c2ccccc2)CO1]

To a suspension of (4R)-2-oxooxazolidine-4-carboxylic acid (0.150 g, 1.14 mmol) in dry THF (1.5 ml) was added a drop of dimethylformamide followed by a dropwise addition of oxalyl chloride (0.11 ml, 1.25 mmol). The reaction mixture was stirred at ambient temperature for 20 minutes. The above prepared solution was added dropwise to a suspension of N-phenylhydroxylamine (0.158 g, 1.37 mmol) and $Na_2CO_3$ (0.182 g, 1.72 mmol) in THF (1.5 ml) at 0° C. The resulting reaction mixture was stirred at ambient temperature for 1.5 h. The precipitate was filtered off and to the filtrate was added aqueous saturated $NaHCO_3$ and ethyl acetate. The phases were separated and the aqueous phase was extracted with EtOAc (3×). The combined organic phases were dried over anhydrous $MgSO_4$ and evaporated under reduced pressure. The crude product was purified by silica gel chromatography (0-5% MeOH in DCM) to afford (4R)—N-hydroxy-2-oxo-N-phenyl-oxazolidine-4-carboxamide (0.1802 g) as a beige solid.

$^1$H NMR (400 MHz, $CD_3OD$) δ 7.71-7.61 (m, 2H), 7.45-7.34 (m, 2H), 7.26-7.18 (m, 1H), 5.04 (dd, J=9.2, 5.0 Hz, 1H), 4.78 (t, J=9.2 Hz), 4.50 (dd, J=8.8, 5.0 Hz, 1H).

Example 12 preparation of tert-butyl N-[(4R)-3-oxo-2-phenyl-isoxazolidin-4-yl]carbamate

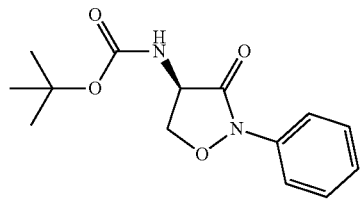 [SMILES: CC(C)(C)OC(=O)N[C@@H]1CON(c2ccccc2)C1=O]

To a solution of (4R)—N-hydroxy-2-oxo-N-phenyl-oxazolidine-4-carboxamide (0.100 g, 0.450 mmol) in THF (1.0 ml) and water (0.3 ml) was added triethylamine (0.127 ml, 0.900 mmol). The resulting solution was stirred in a closed vial at 70° C. for 2.5 h. The reaction mixture was cooled to ambient temperature and di-tertbutyldicarbonate (0.111 g, 0.495 mmol) was added. The reaction mixture was stirred for another 1.5 h, diluted with water and extracted with EtOAc (3×). The combined organic phases were dried over anhydrous $MgSO_4$ and evaporated under reduced pressure. The crude product was purified by silica gel chromatography (0-23% EtOAc in cyclohexane) to afford tert-butyl N-[(4R)-3-oxo-2-phenyl-isoxazolidin-4-yl]carbamate (0.0902 g) as a beige solid.

$^1$H NMR (400 MHz, $CDCl_3$) δ 7.73-7.67 (m, 2H), 7.43-7.36 (m, 2H), 7.22-7.16 (m, 1H), 5.23 (br, 1H), 5.00-4.89 (m, 1H), 4.85-4.74 (m, 1H), 4.19 (dd, J=8.5, 11.0 Hz, 1H), 1.48 (s, 9H).

Example 13 preparation of N-hydroxy-N-methyl-2-oxo-oxazolidine-4-carboxamide

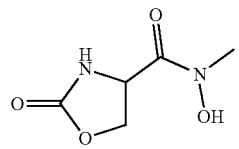

To a suspension of 2-oxooxazolidine-4-carboxylic acid (0.200 g, 1.53 mmol) in dry 1,2-dichloroethane (2.0 ml) was added a drop of dimethylformamide followed by a dropwise addition of oxalyl chloride (0.144 ml, 1.68 mmol). The reaction mixture was stirred at ambient temperature for 30 minutes. The above prepared solution was added dropwise to a suspension prepared by mixing triethylamine (0.52 ml, 3.66 mmol) and N-methylhydroxylamine hydrochloride (0.143 g, 1.68 mmol) in 1,2-dichloroethane (2.0 ml). The resulting brownish reaction mixture was stirred at ambient temperature for 1 h. The reaction mixture was evaporated under reduced pressure and the residue was suspended in THF (8.0 ml). This suspension was heated at 50° C. for 10 min and the remaining brown precipitate was filtered off. The filtrate was evaporated under reduced pressure to provide the crude product as a sticky yellow oil. Purification by silica gel chromatography (0-10% MeOH in DCM) afforded N-hydroxy-N-methyl-2-oxo-oxazolidine-4-carboxamide (0.120 g) as a colorless oil which solidified upon standing.

$^1$H NMR (400 MHz, $CD_3OD$) δ 4.87 (dd, J=9.5, 5.1 Hz, 1H), 4.67 (t, J=9.4 Hz, 1H), 4.36 (dd, J=9.0, 5.3 Hz, 1H), 3.23 (s, 3H).

Example 14 preparation of tert-butyl N-(2-methyl-3-oxo-isoxazolidin-4-yl)carbamate

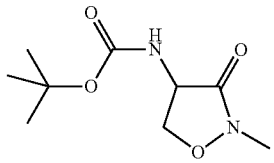

To a solution of N-hydroxy-N-methyl-2-oxo-oxazolidine-4-carboxamide (0.120 g, 0.749 mmol) in a mixture of THF (1.5 ml) and water (0.50 ml) was added triethylamine (0.21 ml, 1.50 mmol) and the resulting solution was stirred at ambient temperature for 18 h. Di-tertbutyldicarbonate (0.173 g, 0.787 mmol) was added and the reaction mixture was stirred for another 2 h. The reaction mixture was diluted with DCM and water, aqueous phase was extracted with DCM (3×) and the combined organic layers were dried over anhydrous $MgSO_4$ and evaporated under reduced pressure. The crude product was purified by silica gel chromatography (0-50% EtOAc in cyclohexane) to afford tert-butyl N-(2-methyl-3-oxo-isoxazolidin-4-yl)carbamate (0.0546 g) as a white powder.

$^1$H NMR (400 MHz, CDCl$_3$) δ 5.32 (br, 1H), 4.71-4.60 (m, 1H), 4.58-4.44 (m, 1H), 3.96 (dd, J=10.3, 8.4 Hz, 1H), 3.17 (s, 3H), 1.41 (s, 9H).

Example 15 preparation of (4R)—N-ethyl-N-hydroxy-2-oxo-oxazolidine-4-carboxamide

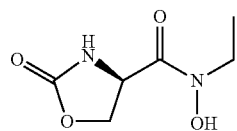

To a suspension of (4R)-2-oxooxazolidine-4-carboxylic acid (10.0 g, 75.9 mmol) in dry THF (50 ml) was added three drops of DMF followed by a dropwise addition of oxalyl chloride (7.31 ml, 83.5 mmol) at 0° C. After the addition the reaction mixture was stirred for another 30 min at ambient temperature. In a separate flask triethylamine (37.2 ml, 266 mmol) was slowly added to a solution of N-ethylhydroxylamine hydrochloride in THF (100 ml). To this formed thick white suspension was added a solution of acid chloride prepared above over 45 min at 0 C. After finishing of addition the reaction mixture was warmed up to ambient temperature, additional THF (50 ml) was added and the reaction mixture was brought to reflux. The remaining precipitate (triethylamine hydrochloride) was filtered off and the filtrate was concentrated under reduced pressure to afford crude product (15.9 g). Quantitative NMR analysis using trimethoxy benzene as an internal standard indicated that the mixture contains (4R)—N-ethyl-N-hydroxy-2-oxo-oxazolidine-4-carboxamide (11.39 g) as the major component. Crystallization of the crude product from methanol afforded (4R)—N-ethyl-N-hydroxy-2-oxo-oxazolidine-4-carboxamide (8.86 g) as a white powder.

$^1$H NMR (400 MHz, D$_2$O) δ 5.01 (dd, J=9.9, 5.9 Hz), 4.77 (t, J=9.2 Hz, 1H), 4.39 (dd, J=9.0, 5.7 Hz, 1H), 3.65 (q, J=7.1 Hz, 2H), 1.16 (t, J=7.1 Hz, 3H).

Example 16 preparation of (4R)-4-amino-2-ethyl-isoxazolidin-3-one hydrochloride

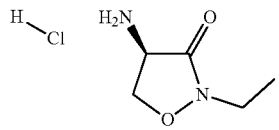

To a suspension of (4R)—N-ethyl-N-hydroxy-2-oxo-oxazolidine-4-carboxamide (13.09 g, 74.8 mmol) in water (35 ml) was added triethylamine (1.05 ml, 7.48 mmol) and the resulting mixture was heated at 70° C. for 2 h (clear solution at this temperature). The reaction mixture was cooled to ambient temperature and 37% aq HCl (7.5 ml, 89.7 mmol) was slowly added. The resulting mixture was evaporated under reduced pressure and the residue dried under vacuum to afford (4R)-4-amino-2-ethyl-isoxazolidin-3-one hydrochloride (13.6 g) as a white powder mixed with 10% of triethylamine hydrochloride. Stereochemical integrity was checked by converting a small portion of the product to tert-butyl N-[(4R)-2-ethyl-3-oxo-isoxazolidin-4-yl]carbamate (see example 10) by treating hydrochloride salt with triethylamine (1.1 eq) and di-tertbutyldicarbonate (1.2 eq) in THF. Chiral HPLC analysis (Chiralpack IA, heptane:ethanol=80:20, 1 ml/min, retention time 2.82 minutes (minor enantiomer 0%) and 4.10 minutes (major enantiomer 100%)) $^1$H NMR (400 MHz, D$_2$O) δ 4.58 (t, J=8.1 Hz, 1H), 4.10-4.04 (m, 1H), 4.02-3.96 (m, 1H), 3.68-3.51 (m, 2H), 1.18 (t, J=7.0 Hz, 3H).

Alternatively, the Title Compound can be Obtained by Carrying Out the Following Procedure:

At 0-5° C., a suspension of sodium (4R)-2-oxooxazolidine-4-carboxylate (10.06 g, 85.1% purity, 55.9 mmol) and Aliquat® 336 (0.56 g, 1.39 mmol) in 2-methyl-tetrahydrofurane (70 ml) was successively treated with N,N-dimethylformamide (0.21 g, 2.87 mmol) and oxalyl chloride (8.58 g, 67.6 mmol). The reaction mixture was stirred for 90 min at ambient temperature and added dropwise to a suspension of triethylamine (13.1 g, 0.129 mol) and N-ethylhydroxylamine hydrochloride (4.99 g, 89.9% purity, 0.046 mol) in 2-methyl-tetrahydrofurane (40 ml) at −5° C. The resulting brownish mixture was stirred for 30 min at ambient temperature and washed with water (2×75 ml). The combined aqueous layers containing the intermediate (4R)—N-ethyl-N-hydroxy-2-oxo-oxazolidine-4-carboxamide were heated to 45° C., treated with aq. NaOH (30% (w/w) soln., 2.95 g, 22.1 mmol), and stirred for additional 60 min. A part of water (35 g) was removed by distillation and the mixture was treated with aq. HCl (32% (w/w), 9.3 g, 81.6 mmol) to reach pH 1. The distillation was continued to finally obtain crude (4R)-4-amino-2-ethyl-isoxazolidin-3-one hydrochloride (56 g, ca. 9% solution in water as analyzed by quantitative $^1$H-NMR analysis).

Alternatively, the Title Compound can be Obtained by Carrying Out the Following Procedure:

A suspension of sodium (4R)-2-oxooxazolidine-4-carboxylate (10.0 g, 95.0% purity, 62.1 mmol) and Aliquat® 336 (0.66 g, 1.63 mmol) in ethyl acetate (80 ml) was successively treated with HCl in dioxane (4 M soln., 3.1 ml, 12.4 mmol) and N,N-dimethylformamide (0.23 g, 3.15 mmol). The resulting mixture was treated with a solution of thionyl chloride (9.0 g, 75.6 mmol) in ethyl acetate (10 ml) at 10-15° C. within 70 min, stirred at ambient temperature for additional 2 h and added dropwise to a suspension of triethylamine (15.4 g, 0.152 mol) and N-ethylhydroxylamine hydrochloride (6.4 g, 77.0% purity, 50.5 mol) in ethyl acetate (65 ml) at 0-5° C. The resulting brownish mixture was stirred at ambient temperature for 60 min and washed with water (2×50 ml). The combined aqueous layers containing the intermediate (4R)—N-ethyl-N-hydroxy-2-oxo-oxazolidine-4-carboxamide were heated to 40° C., treated with aq. NaOH (30% (w/w) soln., 13.6 g, 0.102 mol), and stirred for additional 60 min. A part of water (25 g) was removed by distillation and the mixture was treated with aq. HCl (32% (w/w) soln., 12.2 g, 0.107 mol) to reach pH 1. The mixture was completely evaporated to obtain crude (4R)-4-amino-2-ethyl-isoxazolidin-3-one hydrochloride (27.1 g, ca. 11.8% purity as determined by quantitative $^1$H NMR analysis) as orange solid.

Example 17 preparation of (4R)—N-benzyl-N-hydroxy-2-oxo-oxazolidine-4-carboxamide

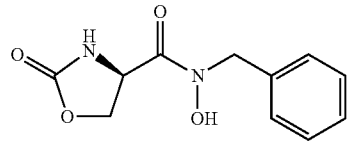 [SMILES: O=C1N[C@@H](C(=O)N(O)Cc2ccccc2)CO1]

To a solution of (4R)-2-oxooxazolidine-4-carboxylic acid (0.300 g, 2.29 mmol) in dry tetrahydrofuran (3.0 ml) was added 2 drops of DMF followed by oxalyl chloride (0.22 ml, 2.52 mmol) at 0° C. After stirring at rt for 20 min the resulting solution was slowly added at 0° C. to a suspension of sodium carbonate (0.603 g, 7.1 mmol) and N-benzylhydroxylamine hydrochloride (0.438 g, 2.75 mmol) in tetrahydrofuran (6.0 ml). The reaction mixture was stirred at rt for 2 h. The remaining precipitate was filtered off and aq sat. NaHCO₃ was added to the filtrate. The aqueous phase was extracted with EtOAc (3×) and combined organic layers were dried over MgSO4 and evaporated under reduced pressure. The crude product was purified by silica gel chromatography (0-5% MeOH in dichloromethane) to afford (4R)—N-benzyl-N-hydroxy-2-oxo-oxazolidine-4-carboxamide (0.393 g) as a white powder.

$^1$H NMR (400 MHz, CD$_3$OD) δ 7.38-7.27 (m, 5H), 4.88 (dd, J=9.7, 5.3 Hz, 1H), 4.77 (s, 2H), 4.65 (t, J=9.4 Hz, 1H), 4.32 (dd, J=9.0, 5.3 Hz, 1H), 3.35 (s, 1H).

Example 18 preparation of tert-butyl N-[(4R)-2-benzyl-3-oxo-isoxazolidin-4-yl]carbamate

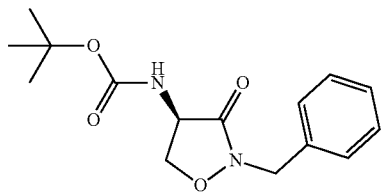 [SMILES: CC(C)(C)OC(=O)N[C@@H]1CON(Cc2ccccc2)C1=O]

To a solution of (4R)—N-benzyl-N-hydroxy-2-oxo-oxazolidine-4-carboxamide (0.200 g, 0.847 mmol) in a mixture of THF (1.0 ml) and water (2.0 ml) was added triethylamine (0.24 ml, 1.69 mmol). The resulting reaction mixture was heated in a sealed vial at 70° C. for 3 h. The reaction mixture was diluted with water and extracted with dichloromethane (3×). The combined organic layers were dried over MgSO4 and evaporated under reduced pressure. The crude residue was purified by silica gel chromatography (0-40% EtOAc in CyH) to afford tert-butyl N-[(4R)-2-benzyl-3-oxo-isoxazolidin-4-yl]carbamate (0.136 g) as a colorless oil which solidified upon standing.

$^1$H NMR (400 MHz, CD$_3$OD) δ 7.39-7.29 (m, 5H), 5.16 (br, 1H), 4.78 (d, J=15.4 Hz, 1H), 4.75-4.68 (m, 1H), 4.68 (d, J=15.8 Hz, 1H), 4.64-4.55 (m, 1H), 3.94 (dd, J=10.6, 8.4 Hz, 1H), 1.46 (s, 9H).

Example 19 preparation of sodium (4R)-2-oxooxazolidine-4-carboxylate

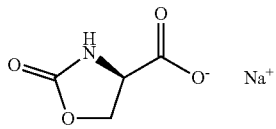

(2R)-2-(Ethoxycarbonylamino)-3-hydroxy-propanoic acid (80 g, 0.452 mol) was dissolved in ethanol (800 ml) at 35° C. and treated in several portions with sodium hydroxide (24.0 g, 0.600 mol, microprills) at 25° C. After complete addition, the reaction mixture was warmed to 40° C. and stirred overnight. The precipitated solid was filtered off, washed with ethanol, and dried under reduced pressure to give sodium (4R)-2-oxooxazolidine-4-carboxylate (50.7 g) as a white powder containing ca. 20% of the residual solvent.

$^1$H NMR (400 MHz, D$_2$O) δ 4.57-4.63 (m, 1H), 4.25-4.31 (m, 2H).

$^1$H NMR (400 MHz, D$_2$O/DMSO-d6 4:1) δ 4.63 (dd, J=9.6, 8.5 Hz, 1H), 4.33 (dd, J=8.5, 5.8 Hz, 1H), 4.27 (dd, J=9.6, 5.7 Hz, 1H).

Alternatively, the Title Compound can be Obtained by Carrying Out the Following Procedure:

At 21° C., a solution of methyl (4R)-2-oxooxazolidine-4-carboxylate (20.0 g, 91.0% purity, 0.125 mol) in acetonitrile (100 g) was treated with sodium hydroxide (microprills) in methanol (16.2% (w/w) soln., 37.0 g, 0.150 mol) within 60 min and stirred at the ambient temperature for additional 30 min. The resulting precipitate was filtered off, washed with acetonitrile (3×25 g) and dried at 100° C. under vacuum to give sodium (4R)-2-oxooxazolidine-4-carboxylate (20 g, 83.2% purity as determined by quantitative $^1$H NMR analysis) as slightly yellow solid.

Example 20 preparation of lithium 2-oxooxazolidine-4-carboxylate

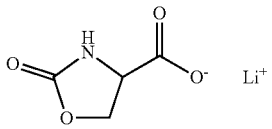

At 0-5° C., a solution of methyl 2-oxooxazolidine-4-carboxylate (1.0 g, 6.89 mmol) in 2-methyl-tetrahydrofurane (5 g) was treated with a solution of lithium hydroxide (0.167 g, 6.97 mmol) in methanol (2 ml) within 15 min. After complete addition, more methanol (1 ml) was added and the reaction mixture was stirred at 0-5° C. for additional 60 min. The resulting precipitate was filtered off and dried under vacuum to give lithium 2-oxooxazolidine-4-carboxylate (610 mg) as a white solid containing ca. 3% of the residual solvent.

$^1$H NMR (400 MHz, D$_2$O) δ 4.57-4.63 (m, 1H), 4.25-4.31 (m, 2H).

The invention claimed is:
1. A process for the preparation of a compound of formula (I)

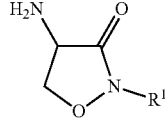
(I)

comprising
i. reacting a compound of formula (II) or a salt thereof

(II)

with a compound of formula (V)

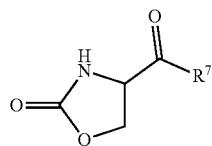
(V)

in the presence of a suitable base to produce a compound of formula (VI)

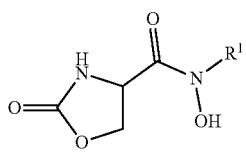
(VI)

and
ii. converting the compound of formula (VI) to a compound of formula (I) by treatment of the compound of formula (VI) with an aqueous base
wherein
$R^1$ is $C_1$-$C_8$alkyl, $C_1$-$C_8$haloalkyl, $C_3$-$C_6$ cycloalkyl, aryl or aryl substituted by one to five $R^{11}$, or aryl-$C_1$-$C_4$alkylene or aryl-$C_1$-$C_4$alkylene substituted by one to five $R^{11}$; and
each $R^{11}$ is independently $C_1$-$C_4$alkyl, $C_1$-$C_4$haloalkyl, $C_1$-$C_4$alkoxy, $C_1$-$C_4$haloalkoxy, cyano or halogen;
$R^7$ is hydroxy or halogen or OM where M is Na, K, Li.
2. A compound of formula (V)

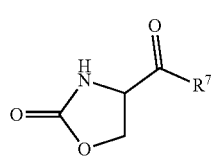
(V)

wherein $R^7$ is is OM where M is Na, K, Li.

3. A compound of formula (VI)

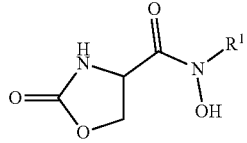
(VI)

wherein
$R^1$ is $C_1$-$C_8$alkyl, $C_1$-$C_8$haloalkyl, $C_3$-$C_6$ cycloalkyl, aryl or aryl substituted by one to five $R^{11}$, or aryl-$C_1$-$C_4$alkylene or aryl-$C_1$-$C_4$alkylene substituted by one to five $R^{11}$;
each $R^{11}$ is independently $C_1$-$C_4$alkyl, $C_1$-$C_4$haloalkyl, $C_1$-$C_4$alkoxy, $C_1$-$C_4$haloalkoxy, cyano or halogen;
or a salt or N-oxide thereof.
4. The process according to claim 1, wherein the process further comprises reacting the compound of formula (I) with a second compound, wherein the second compound comprises a carboxylic acid, acid halide, ester or thioester functional group, and the reaction comprises reacting the amine functional group of the compound of formula (I) with the carboxylic acid, acid halide, ester or thioester functional group of the second compound such that the compound of formula (I) is coupled to the second compound via an amide functional group, or wherein the second compound comprises a dicarbonate group, and the reaction comprises reacting the amine functional group of the compound of formula (I) with the dicarbonate group of the second compound, such that the compound of formula (I) is coupled to the second compound via a carbamate functional group.
5. The process according to claim 4, wherein the second compound is a compound of formula (XII)

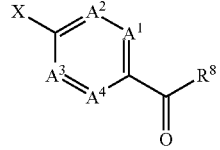
(XII)

and the process results in a compound of formula (VIII)

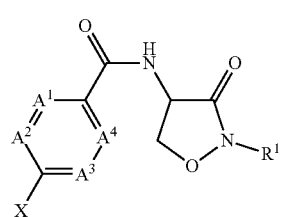
(VIII)

wherein
X is a leaving group selected from halogen, $C_1$-$C_8$alkylsulfonyloxy, $C_1$-$C_8$haloalkylsulfonyloxy, $C_1$-$C_8$arylsulfonyloxy or $C_1$-$C_8$arylsulfonyloxy substituted by one to five $R^{11}$, or a phosphonate ester, cyano, formyl, acetyl, C(O)CH=C($R^3$)$R^4$, C(O)CH$_2$C(OH)($R^3$)$R^4$ or group A

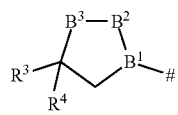

(A)

—B¹—B²—B³— is —C=N—O—, —C=N—CH₂—, —C=CH₂—O— or —N—CH₂—CH₂—;

A¹, A², A³ and A⁴ are independently of one another C—H, C—R⁵, or nitrogen;

R³ is $C_1$-$C_8$haloalkyl;

R⁴ is aryl or aryl substituted by one to three R⁶, or R⁴ is heterocyclyl or heterocyclyl substituted by one to three R⁶;

each R⁵ is independently halogen, cyano, nitro, $C_1$-$C_8$alkyl, $C_3$-$C_8$cycloalkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, $C_1$-$C_8$alkoxy, $C_1$-$C_8$haloalkoxy, $C_1$-$C_8$alkoxycarbonyl-, or two R⁵ on adjacent carbon atoms together form a —CH=CH—CH=CH— bridge or a —N=CH—CH=CH— bridge;

each R⁶ is independently halogen, cyano, nitro, $C_1$-$C_8$alkyl, $C_1$-$C_8$haloalkyl, $C_1$-$C_8$alkoxy, or $C_1$-$C_8$haloalkoxy;

R⁸ is hydroxy, $C_1$-$C_6$alkoxy, fluoro, chloro, bromo, or SR$^x$ wherein R$^x$ is H, $C_1$-$C_6$alkyl, imidazole or pyrrole; and each R¹¹ is independently $C_1$-$C_4$alkyl, $C_1$-$C_4$haloalkyl, $C_1$-$C_4$alkoxy, $C_1$-$C_4$haloalkoxy, cyano or halogen;

R¹ is $C_1$-$C_8$alkyl, $C_1$-$C_8$haloalkyl, aryl or aryl substituted by one to five R¹¹, or aryl-$C_1$-$C_4$alkylene or aryl-$C_1$-$C_4$alkylene substituted by one to five R¹¹; and each R¹¹ is independently $C_1$-$C_4$alkyl, $C_1$-$C_4$haloalkyl, $C_1$-$C_4$alkoxy, $C_1$-$C_4$haloalkoxy, cyano or halogen;

or the second compound is a compound of formula (XIII)

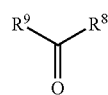

(XIII)

wherein and the process results in a compound of formula (IX)

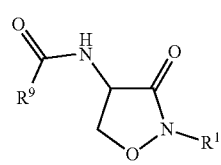

(IX)

wherein

R¹ is $C_1$-$C_8$alkyl, $C_1$-$C_8$haloalkyl, aryl or aryl substituted by one to five R¹¹, or aryl-$C_1$-$C_4$alkylene or aryl-$C_1$-$C_4$alkylene substituted by one to five R¹¹; and R⁹ is hydrogen, $C_1$-$C_8$alkyl or $C_1$-$C_8$haloalkyl and R⁸ is as defined for compound of formula (XII);

each R¹¹ is independently $C_1$-$C_4$alkyl, $C_1$-$C_4$haloalkyl, $C_1$-$C_4$alkoxy, $C_1$-$C_4$haloalkoxy, cyano or halogen;

or the second compound is a compound of formula (XIVa) or (XIVb)

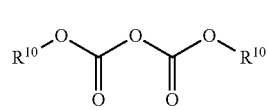

(XIVa)

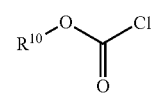

(XIVb)

and the process results in a compound of formula X

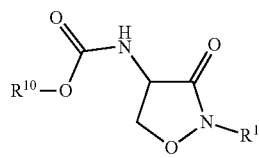

(X)

wherein

R¹ is $C_1$-$C_8$alkyl, $C_1$-$C_8$haloalkyl, aryl or aryl substituted by one to five R¹¹, or aryl-$C_1$-$C_4$alkylene or aryl-$C_1$-$C_4$alkylene substituted by one to five R¹¹;

each R¹⁰ is independently $C_1$-$C_8$alkyl, $C_1$-$C_8$haloalkyl, aryl-$C_1$-$C_4$alkylene- or aryl-$C_1$-$C_4$alkylene-substituted by one to five R¹¹;

each R¹¹ is independently $C_1$-$C_4$alkyl, $C_1$-$C_4$haloalkyl, $C_1$-$C_4$alkoxy, $C_1$-$C_4$haloalkoxy, cyano or halogen.

* * * * *